US008632562B2

(12) United States Patent
Pal et al.

(10) Patent No.: US 8,632,562 B2
(45) Date of Patent: Jan. 21, 2014

(54) EMBOLIC PROTECTION DEVICE

(75) Inventors: Dharmendra Pal, Wilmington, MA (US); Mark A. Magnuson, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 919 days.

(21) Appl. No.: 11/542,609

(22) Filed: Oct. 2, 2006

(65) Prior Publication Data

US 2007/0088383 A1    Apr. 19, 2007

Related U.S. Application Data

(60) Provisional application No. 60/723,255, filed on Oct. 3, 2005.

(51) Int. Cl.
| | |
|---|---|
| A61M 16/00 | (2006.01) |
| A61M 29/02 | (2006.01) |
| A61F 2/01 | (2006.01) |
| A61M 1/34 | (2006.01) |

(52) U.S. Cl.
USPC .......................................... 606/200; 606/194

(58) Field of Classification Search
USPC .................. 606/113, 114, 127, 128, 159, 200
See application file for complete search history.

(56) References Cited

U.S. PATENT DOCUMENTS

| | | | |
|---|---|---|---|
| 3,108,593 A | 10/1963 | Glassman | |
| 3,334,629 A | 8/1967 | Cohn | |
| 3,472,230 A | 10/1969 | Fogarty | |
| 3,547,103 A | 12/1970 | Cook | |
| 3,635,223 A | 1/1972 | Klieman | |
| 3,923,065 A | 12/1975 | Nozick et al. | |
| 3,952,747 A | 4/1976 | Kimmell, Jr. | |
| 3,978,863 A | 9/1976 | Fettel et al. | |
| 3,996,938 A | 12/1976 | Clark, III | |
| 4,425,908 A | 1/1984 | Simon | |

(Continued)

FOREIGN PATENT DOCUMENTS

| | | |
|---|---|---|
| DE | 34 29 850 A1 | 2/1986 |
| EP | 1127556 A2 | 8/2001 |

(Continued)

OTHER PUBLICATIONS

Rubicon Embolic Filter, The Next Generation of EM, Rubicon Medical, www.rubiconmed.com.

(Continued)

*Primary Examiner* — Thomas McEvoy
*Assistant Examiner* — Sarah W Aleman
(74) *Attorney, Agent, or Firm* — Brinks Gilson & Lione

(57) ABSTRACT

An embolic protection device for deployment in a body vessel is provided for filtering emboli within the body vessel. The embolic protection device generally includes a filter having a plurality of openings formed therethrough and an extraction element configured to be movable with respect to the filter between a non-extraction position and an extraction position. The extraction element is located distally of the filter when in the non-extraction position so as to allow the filter to open into an expanded state to collect the emboli. Additionally, the extraction element is disposed about at least a portion of the filter when in the extraction position so as to close the filter into a collapsed state and to permit the embolic protection device to be extracted from the body vessel.

16 Claims, 9 Drawing Sheets

(56) References Cited

U.S. PATENT DOCUMENTS

| | | | |
|---|---|---|---|
| 4,456,000 A | 6/1984 | Schjeldahl et al. | |
| 4,494,531 A | 1/1985 | Gianturco | |
| 4,548,206 A | 10/1985 | Osborne | |
| 4,561,439 A | 12/1985 | Bishop et al. | |
| 4,562,039 A | 12/1985 | Koehler | |
| 4,604,094 A | 8/1986 | Shook | |
| 4,619,246 A | 10/1986 | Molgaard-Nielsen et al. | |
| 4,643,184 A | 2/1987 | Mobin-Uddin | |
| 4,646,736 A | 3/1987 | Auth | |
| 4,650,472 A | 3/1987 | Bates | |
| 4,665,906 A | 5/1987 | Jervis | |
| 4,669,464 A | 6/1987 | Sulepov | |
| 4,688,553 A | 8/1987 | Metals | |
| 4,723,549 A | 2/1988 | Wholey et al. | |
| 4,727,873 A | 3/1988 | Mobin-Uddin | |
| 4,732,152 A | 3/1988 | Wallsten et al. | |
| 4,817,600 A | 4/1989 | Herms et al. | |
| 4,824,435 A | 4/1989 | Giesy et al. | |
| 4,832,055 A | 5/1989 | Palestrant | |
| 4,846,794 A * | 7/1989 | Hertzer | 604/83 |
| 4,848,343 A | 7/1989 | Wallsten et al. | |
| 4,873,978 A | 10/1989 | Ginsburg | |
| 4,943,297 A | 7/1990 | Saveliev et al. | |
| 4,957,501 A | 9/1990 | Lahille et al. | |
| 4,990,156 A | 2/1991 | Lefebvre | |
| 4,998,916 A | 3/1991 | Hammerslag et al. | |
| 5,053,008 A | 10/1991 | Bajaj | |
| 5,059,205 A | 10/1991 | El-Nounou et al. | |
| 5,069,226 A | 12/1991 | Yamauchi et al. | |
| 5,078,726 A | 1/1992 | Kreamer | |
| 5,100,423 A | 3/1992 | Fearnot | |
| 5,108,418 A | 4/1992 | Lefebvre | |
| 5,108,419 A * | 4/1992 | Reger et al. | 606/200 |
| 5,112,347 A | 5/1992 | Taheri | |
| 5,129,890 A | 7/1992 | Bates et al. | |
| 5,133,733 A | 7/1992 | Rasmussen et al. | |
| 5,147,379 A | 9/1992 | Sabbaghian et al. | |
| 5,152,777 A | 10/1992 | Goldberg | |
| 5,160,342 A | 11/1992 | Reger | |
| 5,163,927 A | 11/1992 | Woker et al. | |
| 5,203,772 A | 4/1993 | Hammerslag et al. | |
| 5,234,458 A | 8/1993 | Metais | |
| 5,242,462 A | 9/1993 | El-Nounou | |
| 5,243,996 A | 9/1993 | Hall | |
| 5,251,640 A | 10/1993 | Osborne | |
| 5,263,964 A | 11/1993 | Purdy | |
| 5,300,086 A | 4/1994 | Gory et al. | |
| 5,324,304 A | 6/1994 | Rasmussen | |
| 5,329,942 A | 7/1994 | Gunther et al. | |
| 5,344,427 A | 9/1994 | Cottenceau et al. | |
| 5,350,397 A | 9/1994 | Palermo et al. | |
| 5,350,398 A | 9/1994 | Pavcnik et al. | |
| 5,364,345 A | 11/1994 | Lowery et al. | |
| 5,370,657 A | 12/1994 | Irie | |
| 5,375,612 A | 12/1994 | Cottenceau et al. | |
| 5,383,887 A | 1/1995 | Nadal | |
| 5,413,586 A | 5/1995 | Dibie et al. | |
| 5,415,630 A | 5/1995 | Gory et al. | |
| 5,417,708 A | 5/1995 | Hall et al. | |
| 5,451,233 A | 9/1995 | Yock | |
| 5,458,573 A | 10/1995 | Summers | |
| 5,522,881 A | 6/1996 | Lentz | |
| 5,527,338 A | 6/1996 | Purdy | |
| 5,531,788 A | 7/1996 | Dibie et al. | |
| 5,549,551 A | 8/1996 | Peacock et al. | |
| 5,549,626 A | 8/1996 | Miller et al. | |
| 5,556,414 A | 9/1996 | Turi | |
| 5,562,698 A | 10/1996 | Parker | |
| 5,571,135 A * | 11/1996 | Fraser et al. | 623/1.12 |
| 5,591,195 A | 1/1997 | Taheri et al. | |
| 5,601,595 A | 2/1997 | Smith | |
| 5,624,461 A | 4/1997 | Mariant | |
| 5,626,605 A | 5/1997 | Irie et al. | |
| 5,630,797 A | 5/1997 | Diedrich et al. | |
| 5,634,942 A | 6/1997 | Chevillon et al. | |
| 5,649,953 A | 7/1997 | Lefebvre | |
| 5,662,703 A | 9/1997 | Yurek et al. | |
| 5,669,933 A | 9/1997 | Simon et al. | |
| 5,681,347 A | 10/1997 | Cathcart et al. | |
| 5,690,642 A | 11/1997 | Osborne et al. | |
| 5,690,667 A | 11/1997 | Gia | |
| 5,693,067 A | 12/1997 | Purdy | |
| 5,693,087 A | 12/1997 | Parodi | |
| 5,695,518 A | 12/1997 | Laerum | |
| 5,695,519 A | 12/1997 | Summers et al. | |
| 5,700,253 A | 12/1997 | Parker | |
| 5,709,704 A | 1/1998 | Nott et al. | |
| 5,713,853 A | 2/1998 | Clark et al. | |
| 5,720,764 A | 2/1998 | Naderlinger | |
| 5,725,550 A | 3/1998 | Nadal | |
| 5,738,667 A | 4/1998 | Solar | |
| 5,746,767 A | 5/1998 | Smith | |
| 5,755,772 A | 5/1998 | Evans et al. | |
| 5,755,790 A | 5/1998 | Chevillon et al. | |
| 5,766,203 A | 6/1998 | Imran et al. | |
| 5,769,816 A | 6/1998 | Barbut et al. | |
| 5,769,871 A | 6/1998 | Mers et al. | |
| 5,795,322 A | 8/1998 | Boudewijn | |
| 5,800,457 A | 9/1998 | Gelbfish et al. | |
| 5,800,525 A | 9/1998 | Bachinski et al. | |
| 5,810,874 A | 9/1998 | Lefebvre | |
| 5,814,027 A | 9/1998 | Hassett et al. | |
| 5,814,064 A | 9/1998 | Daniel et al. | |
| 5,820,592 A | 10/1998 | Hammerslag | |
| 5,827,324 A | 10/1998 | Cassell et al. | |
| 5,830,230 A | 11/1998 | Berryman et al. | |
| 5,836,968 A | 11/1998 | Simon et al. | |
| 5,836,969 A | 11/1998 | Kim et al. | |
| 5,846,260 A | 12/1998 | Maahs | |
| 5,853,420 A | 12/1998 | Chevillon et al. | |
| 5,876,367 A | 3/1999 | Kaganov et al. | |
| 5,893,869 A | 4/1999 | Barnhart et al. | |
| 5,895,391 A | 4/1999 | Farnholtz | |
| 5,895,399 A | 4/1999 | Barbut et al. | |
| 5,895,410 A | 4/1999 | Forber et al. | |
| 5,908,435 A | 6/1999 | Samuels | |
| 5,910,154 A | 6/1999 | Tsugita et al. | |
| 5,911,702 A | 6/1999 | Romley et al. | |
| 5,911,704 A | 6/1999 | Humes | |
| 5,911,717 A | 6/1999 | Jacobsen et al. | |
| 5,911,734 A | 6/1999 | Tsugita et al. | |
| 5,919,224 A | 7/1999 | Thompson et al. | |
| 5,925,062 A | 7/1999 | Purdy | |
| 5,925,063 A | 7/1999 | Khosravi | |
| 5,928,260 A | 7/1999 | Chine et al. | |
| 5,928,261 A | 7/1999 | Ruiz | |
| 5,938,683 A | 8/1999 | Lefebvre | |
| 5,941,896 A | 8/1999 | Kerr | |
| 5,944,728 A | 8/1999 | Bates | |
| 5,947,985 A | 9/1999 | Imran | |
| 5,947,995 A | 9/1999 | Samuels | |
| 5,948,017 A | 9/1999 | Taheri | |
| 5,951,567 A | 9/1999 | Javier, Jr. et al. | |
| 5,954,741 A | 9/1999 | Fox | |
| 5,954,742 A | 9/1999 | Osypka | |
| 5,954,745 A | 9/1999 | Gertler et al. | |
| 5,968,057 A | 10/1999 | Taheri | |
| 5,968,071 A | 10/1999 | Chevillon et al. | |
| 5,972,019 A | 10/1999 | Engelson et al. | |
| 5,976,162 A | 11/1999 | Doan et al. | |
| 5,976,172 A | 11/1999 | Homsma et al. | |
| 5,980,555 A | 11/1999 | Barbut et al. | |
| 5,984,947 A | 11/1999 | Smith | |
| 5,984,965 A | 11/1999 | Knapp et al. | |
| 5,989,281 A | 11/1999 | Barbut et al. | |
| 6,001,118 A | 12/1999 | Daniel et al. | |
| 6,007,557 A | 12/1999 | Ambrisco et al. | |
| 6,007,558 A | 12/1999 | Ravenscloth et al. | |
| 6,010,522 A | 1/2000 | Barbut et al. | |
| 6,013,093 A | 1/2000 | Nott et al. | |
| 6,015,424 A | 1/2000 | Rosenbluth et al. | |
| 6,027,520 A | 2/2000 | Tsugita et al. | |
| 6,036,717 A | 3/2000 | Mers Kelly et al. | |
| 6,036,720 A | 3/2000 | Abrams et al. | |

(56) References Cited

U.S. PATENT DOCUMENTS

| | | | |
|---|---|---|---|
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,745 A | 5/2000 | Gelbfish | |
| 6,059,814 A | 5/2000 | Ladd | |
| 6,063,113 A | 5/2000 | Kavteladze et al. | |
| 6,066,158 A | 5/2000 | Engelson et al. | |
| 6,068,645 A | 5/2000 | Tu | |
| 6,074,357 A | 6/2000 | Kaganov et al. | |
| 6,077,274 A | 6/2000 | Ouchi et al. | |
| 6,080,178 A | 6/2000 | Meglin | |
| 6,083,239 A | 7/2000 | Addis | |
| 6,086,577 A | 7/2000 | Ken et al. | |
| 6,086,605 A | 7/2000 | Barbut et al. | |
| 6,093,199 A | 7/2000 | Brown et al. | |
| 6,096,053 A | 8/2000 | Bates | |
| 6,096,070 A | 8/2000 | Ragheb et al. | |
| 6,099,549 A | 8/2000 | Bosma et al. | |
| 6,106,497 A | 8/2000 | Wang | |
| 6,126,672 A | 10/2000 | Berryman et al. | |
| 6,126,673 A | 10/2000 | Kim et al. | |
| 6,129,739 A | 10/2000 | Khosravi | |
| 6,136,016 A | 10/2000 | Barbut et al. | |
| 6,146,396 A | 11/2000 | Konya et al. | |
| 6,146,404 A | 11/2000 | Kim et al. | |
| 6,152,931 A | 11/2000 | Nadal et al. | |
| 6,152,946 A | 11/2000 | Broome et al. | |
| 6,152,947 A | 11/2000 | Ambrisco et al. | |
| 6,156,061 A | 12/2000 | Wallace et al. | |
| 6,156,062 A | 12/2000 | McGuinness | |
| 6,159,230 A | 12/2000 | Samuels | |
| 6,165,179 A | 12/2000 | Cathcart et al. | |
| 6,165,198 A | 12/2000 | McGurk et al. | |
| 6,165,199 A | 12/2000 | Barbut | |
| 6,165,200 A | 12/2000 | Tsugita et al. | |
| 6,168,579 B1 | 1/2001 | Tsugita et al. | |
| 6,168,603 B1 | 1/2001 | Leslie et al. | |
| 6,168,610 B1 | 1/2001 | Marin et al. | |
| 6,168,622 B1 | 1/2001 | Mazzocchi | |
| 6,171,327 B1 | 1/2001 | Daniel et al. | |
| 6,171,328 B1 | 1/2001 | Addis | |
| 6,174,318 B1 | 1/2001 | Bates et al. | |
| 6,179,851 B1 | 1/2001 | Barbut et al. | |
| 6,179,859 B1 | 1/2001 | Bates et al. | |
| 6,179,860 B1 | 1/2001 | Fulton, III et al. | |
| 6,179,861 B1 | 1/2001 | Khosravi et al. | |
| 6,187,025 B1 | 2/2001 | Machek | |
| 6,193,739 B1 | 2/2001 | Chevillon et al. | |
| 6,203,561 B1 | 3/2001 | Ramee et al. | |
| 6,206,931 B1 | 3/2001 | Cook et al. | |
| 6,214,025 B1 | 4/2001 | Thistle et al. | |
| 6,214,026 B1 | 4/2001 | Lepak et al. | |
| 6,221,091 B1 | 4/2001 | Khosravi | |
| 6,224,620 B1 | 5/2001 | Maahs | |
| 6,231,588 B1 | 5/2001 | Zadno-Azizi | |
| 6,231,589 B1 | 5/2001 | Wessman et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,241,746 B1 | 6/2001 | Bosma et al. | |
| 6,245,012 B1 | 6/2001 | Kleshinski | |
| 6,245,087 B1 | 6/2001 | Addis | |
| 6,245,088 B1 | 6/2001 | Lowery | |
| 6,245,089 B1 | 6/2001 | Daniel et al. | |
| 6,251,092 B1 | 6/2001 | Qin et al. | |
| 6,251,122 B1 | 6/2001 | Tsukernik | |
| 6,254,550 B1 | 7/2001 | McNamara et al. | |
| 6,254,633 B1 | 7/2001 | Pinchuk et al. | |
| 6,258,026 B1 | 7/2001 | Ravenscroft et al. | |
| 6,258,115 B1 | 7/2001 | Dubrul | |
| 6,258,120 B1 | 7/2001 | McKenzie et al. | |
| 6,261,305 B1 | 7/2001 | Marotta et al. | |
| 6,264,672 B1 | 7/2001 | Fisher | |
| 6,267,776 B1 | 7/2001 | O'Connell | |
| 6,267,777 B1 | 7/2001 | Bosma et al. | |
| 6,273,900 B1 | 8/2001 | Nott et al. | |
| 6,273,901 B1 | 8/2001 | Whitcher et al. | |
| 6,277,125 B1 | 8/2001 | Barry et al. | |
| 6,277,126 B1 | 8/2001 | Barry et al. | |
| 6,277,138 B1 | 8/2001 | Levinson et al. | |
| 6,277,139 B1 | 8/2001 | Levinson et al. | |
| 6,280,451 B1 | 8/2001 | Bates et al. | |
| 6,287,321 B1 | 9/2001 | Jang | |
| 6,290,710 B1 * | 9/2001 | Cryer et al. | 606/200 |
| 6,299,604 B1 | 10/2001 | Ragheb et al. | |
| 6,306,163 B1 | 10/2001 | Fitz | |
| 6,309,399 B1 | 10/2001 | Barbut et al. | |
| 6,312,444 B1 | 11/2001 | Barbut | |
| 6,319,268 B1 | 11/2001 | Ambrisco et al. | |
| 6,325,815 B1 | 12/2001 | Kusleika et al. | |
| 6,325,816 B1 | 12/2001 | Fulton, III et al. | |
| 6,328,755 B1 | 12/2001 | Marshall | |
| 6,331,183 B1 | 12/2001 | Suon | |
| 6,331,184 B1 | 12/2001 | Abrams | |
| 6,334,864 B1 | 1/2002 | Amplatz et al. | |
| 6,336,934 B1 | 1/2002 | Gilson et al. | |
| 6,338,739 B1 | 1/2002 | Datta et al. | |
| 6,340,364 B2 | 1/2002 | Kanesaka | |
| 6,342,062 B1 | 1/2002 | Suon et al. | |
| 6,342,063 B1 | 1/2002 | DeVries et al. | |
| 6,344,048 B1 | 2/2002 | Chin et al. | |
| 6,344,049 B1 | 2/2002 | Levinson et al. | |
| 6,346,116 B1 | 2/2002 | Brooks et al. | |
| 6,348,041 B1 | 2/2002 | Klint | |
| 6,348,063 B1 | 2/2002 | Yassour et al. | |
| 6,350,271 B1 | 2/2002 | Kurz et al. | |
| 6,355,051 B1 | 3/2002 | Sisskind et al. | |
| 6,358,228 B1 | 3/2002 | Tubman et al. | |
| 6,361,545 B1 | 3/2002 | Macoviak et al. | |
| 6,361,546 B1 | 3/2002 | Khosravi | |
| 6,361,547 B1 | 3/2002 | Hieshima | |
| 6,364,895 B1 | 4/2002 | Greenhalgh | |
| 6,364,896 B1 | 4/2002 | Addis | |
| 6,368,338 B1 | 4/2002 | Konya et al. | |
| 6,371,961 B1 | 4/2002 | Osborne et al. | |
| 6,371,969 B1 | 4/2002 | Tsugita et al. | |
| 6,371,970 B1 * | 4/2002 | Khosravi et al. | 606/200 |
| 6,371,971 B1 | 4/2002 | Tsugita et al. | |
| 6,375,670 B1 | 4/2002 | Greenhalgh | |
| 6,379,374 B1 | 4/2002 | Hieshima et al. | |
| 6,380,457 B1 | 4/2002 | Yurek et al. | |
| 6,383,146 B1 | 5/2002 | Klint | |
| 6,383,171 B1 | 5/2002 | Gifford et al. | |
| 6,383,174 B1 | 5/2002 | Eder | |
| 6,383,193 B1 | 5/2002 | Cathcart et al. | |
| 6,383,196 B1 | 5/2002 | Leslie et al. | |
| 6,383,205 B1 | 5/2002 | Samson et al. | |
| 6,383,206 B1 | 5/2002 | Gillick et al. | |
| 6,391,044 B1 | 5/2002 | Yadav et al. | |
| 6,391,045 B1 | 5/2002 | Kim et al. | |
| 6,391,052 B2 | 5/2002 | Buirge et al. | |
| 6,395,014 B1 | 5/2002 | Macoviak et al. | |
| 6,402,771 B1 | 6/2002 | Palmer et al. | |
| 6,402,772 B1 | 6/2002 | Amplatz et al. | |
| 6,409,742 B1 | 6/2002 | Fulton, III et al. | |
| 6,413,235 B1 | 7/2002 | Parodi | |
| 6,416,530 B2 | 7/2002 | DeVries et al. | |
| 6,419,686 B1 | 7/2002 | McLeod et al. | |
| 6,423,052 B1 | 7/2002 | Escano | |
| 6,423,086 B1 | 7/2002 | Barbut et al. | |
| 6,425,909 B1 | 7/2002 | Dieck et al. | |
| 6,428,557 B1 | 8/2002 | Hilaire | |
| 6,428,558 B1 | 8/2002 | Jones et al. | |
| 6,428,559 B1 | 8/2002 | Johnson | |
| 6,432,122 B1 | 8/2002 | Gilson et al. | |
| 6,436,112 B2 | 8/2002 | Wensel et al. | |
| 6,436,120 B1 | 8/2002 | Meglin | |
| 6,436,121 B1 | 8/2002 | Blom | |
| 6,443,926 B1 | 9/2002 | Kletschka | |
| 6,443,971 B1 | 9/2002 | Boylan et al. | |
| 6,443,972 B1 | 9/2002 | Bosma et al. | |
| 6,443,979 B1 | 9/2002 | Stalker et al. | |
| 6,447,530 B1 | 9/2002 | Ostrovsky et al. | |

(56) References Cited

U.S. PATENT DOCUMENTS

| | | |
|---|---|---|
| 6,447,531 B1 | 9/2002 | Amplatz |
| 6,454,775 B1 | 9/2002 | Demarais et al. |
| 6,458,139 B1 | 10/2002 | Palmer et al. |
| 6,458,145 B1 | 10/2002 | Ravenscroft et al. |
| 6,461,370 B1 | 10/2002 | Gray et al. |
| 6,468,290 B1 | 10/2002 | Weldon et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,500 B1 | 11/2002 | Kokish et al. |
| 6,485,501 B1 | 11/2002 | Green |
| 6,485,502 B2 | 11/2002 | Don Michael et al. |
| 6,491,712 B1 | 12/2002 | O'Connor |
| 6,494,895 B2 | 12/2002 | Addis |
| 6,497,709 B1 | 12/2002 | Heath |
| 6,499,487 B1 | 12/2002 | McKenzie et al. |
| 6,500,166 B1 | 12/2002 | Zadno Azizi et al. |
| 6,500,191 B2 | 12/2002 | Addis |
| 6,502,606 B2 | 1/2003 | Klint |
| 6,506,203 B1 | 1/2003 | Boyle et al. |
| 6,506,205 B2 | 1/2003 | Goldberg et al. |
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 | 2/2003 | Blackledge et al. |
| 6,520,983 B1 * | 2/2003 | Colgan et al. ............... 623/1.11 |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,770 B1 | 3/2003 | Lepulu et al. |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 | 4/2003 | Shen et al. |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,227 B2 | 7/2003 | Klint |
| 6,589,230 B2 | 7/2003 | Gia et al. |
| 6,589,263 B1 | 7/2003 | Hopkins et al. |
| 6,589,264 B1 | 7/2003 | Barbut |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,596,011 B2 | 7/2003 | Johnson et al. |
| 6,599,275 B1 | 7/2003 | Fischer, Jr. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,602,280 B2 | 8/2003 | Chobotov |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,611,720 B2 | 8/2003 | Hata et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,160 B1 | 11/2003 | Heesch |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,676,682 B1 | 1/2004 | Tsugita et al. |
| 6,679,902 B1 | 1/2004 | Boyle et al. |
| 6,689,144 B2 | 2/2004 | Gerberding |
| 6,695,813 B1 | 2/2004 | Boyle et al. |
| 6,695,865 B2 | 2/2004 | Boyle et al. |
| 6,702,834 B1 | 3/2004 | Boylan et al. |
| 6,709,450 B2 | 3/2004 | Kang et al. |
| 6,712,835 B2 | 3/2004 | Mazzocchi et al. |
| 6,716,207 B2 | 4/2004 | Farnholtz |
| 6,716,231 B1 | 4/2004 | Rafiee et al. |
| 6,726,701 B2 | 4/2004 | Gilson et al. |
| 6,730,064 B2 | 5/2004 | Ragheb et al. |
| 6,755,856 B2 | 6/2004 | Fierens et al. |
| 6,758,855 B2 | 7/2004 | Fulton, III et al. |
| 6,761,727 B1 | 7/2004 | Ladd |
| 6,773,446 B1 | 8/2004 | Dwyer et al. |
| 6,773,448 B2 | 8/2004 | Kusleika et al. |
| 6,774,278 B1 | 8/2004 | Ragheb et al. |
| 6,780,175 B1 | 8/2004 | Sachdeva et al. |
| 6,793,667 B2 | 9/2004 | Hebert et al. |
| 6,793,668 B1 | 9/2004 | Fisher |
| 6,833,002 B2 | 12/2004 | Stack et al. |
| 6,855,154 B2 | 2/2005 | Abdel-Gawwad |
| 6,866,677 B2 | 3/2005 | Douk et al. |
| 6,866,680 B2 | 3/2005 | Yassour et al. |
| 6,872,211 B2 | 3/2005 | White et al. |
| 6,878,153 B2 * | 4/2005 | Linder et al. ............... 606/200 |

(56) References Cited

U.S. PATENT DOCUMENTS

| | | | |
|---|---|---|---|
| 6,896,691 B2 | 5/2005 | Boylan et al. |
| 6,929,709 B2 | 8/2005 | Smith |
| 6,932,831 B2 | 8/2005 | Forber |
| 6,939,361 B1 | 9/2005 | Kleshinski |
| 6,942,682 B2 | 9/2005 | Vrba et al. |
| 6,955,685 B2 | 10/2005 | Escamilla et al. |
| 6,964,670 B1 | 11/2005 | Shah et al. |
| 6,964,674 B1 | 11/2005 | Matsuura et al. |
| 6,969,396 B2 | 11/2005 | Krolik et al. |
| 6,974,469 B2 | 12/2005 | Broome et al. |
| 6,974,473 B2 | 12/2005 | Barclay et al. |
| 6,986,784 B1 | 1/2006 | Weiser et al. |
| 6,991,641 B2 | 1/2006 | Diaz et al. |
| 7,128,073 B1 | 10/2006 | van der Burg et al. |
| 7,166,120 B2 | 1/2007 | Kusleika |
| 7,174,636 B2 | 2/2007 | Lowe |
| 7,189,249 B2 | 3/2007 | Hart et al. |
| 7,255,687 B2 | 8/2007 | Huang et al. |
| 7,285,130 B2 | 10/2007 | Austin |
| 7,306,619 B1 | 12/2007 | Palmer |
| 7,371,248 B2 | 5/2008 | Dapolito et al. |
| 7,393,358 B2 | 7/2008 | Malewicz |
| 7,604,649 B2 | 10/2009 | McGuckin et al. |
| 7,666,216 B2 | 2/2010 | Hogendijk et al. |
| 7,708,770 B2 * | 5/2010 | Linder et al. ............. 623/1.11 |
| 7,731,722 B2 | 6/2010 | Lavelle et al. |
| 7,766,934 B2 | 8/2010 | Pal et al. |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 | 9/2001 | Okada |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0041928 A1 | 11/2001 | Pavcnik et al. |
| 2001/0044632 A1 | 11/2001 | Daniel et al. |
| 2001/0044634 A1 | 11/2001 | Don Michael et al. |
| 2001/0053921 A1 | 12/2001 | Jang |
| 2002/0002383 A1 | 1/2002 | Sepetka et al. |
| 2002/0002384 A1 | 1/2002 | Gilson et al. |
| 2002/0004667 A1 | 1/2002 | Adams et al. |
| 2002/0016564 A1 | 2/2002 | Courtney et al. |
| 2002/0016609 A1 | 2/2002 | Wensel et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 | 5/2002 | Barbut et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099405 A1 | 7/2002 | Yurek et al. |
| 2002/0099407 A1 | 7/2002 | Becker et al. |
| 2002/0099435 A1 | 7/2002 | Stinson |
| 2002/0103501 A1 | 8/2002 | Diaz et al. |
| 2002/0107541 A1 | 8/2002 | Vale et al. |
| 2002/0111647 A1 | 8/2002 | Khairkhahan et al. |
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |
| 2002/0138097 A1 | 9/2002 | Ostrovsky et al. |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 * | 10/2002 | Demond et al. ............. 606/200 |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0165598 A1 | 11/2002 | Wahr et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0177899 A1 | 11/2002 | Eum et al. |
| 2002/0183781 A1 | 12/2002 | Casey et al. |
| 2002/0183782 A1 | 12/2002 | Tsugita et al. |
| 2002/0183783 A1 | 12/2002 | Shadduck |
| 2002/0188313 A1 | 12/2002 | Johnson et al. |
| 2002/0188314 A1 | 12/2002 | Anderson et al. |
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2002/0198561 A1 | 12/2002 | Amplatz |

(56) References Cited

U.S. PATENT DOCUMENTS

| | | |
|---|---|---|
| 2003/0004536 A1 | 1/2003 | Boylan et al. |
| 2003/0004537 A1* | 1/2003 | Boyle et al. .................. 606/200 |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |
| 2003/0023265 A1 | 1/2003 | Forber |
| 2003/0032976 A1 | 2/2003 | Boucek |
| 2003/0032977 A1 | 2/2003 | Brady |
| 2003/0040772 A1 | 2/2003 | Hyodoh et al. |
| 2003/0045897 A1 | 3/2003 | Huter et al. |
| 2003/0045898 A1 | 3/2003 | Harrison et al. |
| 2003/0050662 A1 | 3/2003 | Michael |
| 2003/0055452 A1 | 3/2003 | Joergensen et al. |
| 2003/0055480 A1 | 3/2003 | Fischell et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0065355 A1 | 4/2003 | Weber |
| 2003/0065356 A1 | 4/2003 | Tsugita et al. |
| 2003/0069596 A1 | 4/2003 | Eskuri |
| 2003/0073979 A1 | 4/2003 | Naimark et al. |
| 2003/0074019 A1 | 4/2003 | Gray et al. |
| 2003/0074054 A1 | 4/2003 | Duerig et al. |
| 2003/0078614 A1 | 4/2003 | Salahieh et al. |
| 2003/0083608 A1 | 5/2003 | Evans et al. |
| 2003/0083692 A1 | 5/2003 | Vrba et al. |
| 2003/0083693 A1 | 5/2003 | Daniel et al. |
| 2003/0088211 A1 | 5/2003 | Anderson et al. |
| 2003/0088266 A1 | 5/2003 | Bowlin |
| 2003/0093110 A1 | 5/2003 | Vale |
| 2003/0093112 A1 | 5/2003 | Addis |
| 2003/0097094 A1 | 5/2003 | Ouriel et al. |
| 2003/0097145 A1 | 5/2003 | Goldberg et al. |
| 2003/0100917 A1 | 5/2003 | Boyle et al. |
| 2003/0100918 A1 | 5/2003 | Duane |
| 2003/0100919 A1 | 5/2003 | Hopkins et al. |
| 2003/0105472 A1 | 6/2003 | McAlister |
| 2003/0105484 A1 | 6/2003 | Boyle et al. |
| 2003/0105486 A1 | 6/2003 | Murphy et al. |
| 2003/0109824 A1 | 6/2003 | Anderson et al. |
| 2003/0109897 A1 | 6/2003 | Walak et al. |
| 2003/0109916 A1 | 6/2003 | Michael |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0120304 A1 | 6/2003 | Kaganov et al. |
| 2003/0125764 A1 | 7/2003 | Brady et al. |
| 2003/0125765 A1 | 7/2003 | Blackledge et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135232 A1 | 7/2003 | Douk et al. |
| 2003/0135233 A1 | 7/2003 | Bates et al. |
| 2003/0139764 A1 | 7/2003 | Levinson et al. |
| 2003/0139765 A1 | 7/2003 | Patel et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0153944 A1 | 8/2003 | Phung et al. |
| 2003/0153945 A1 | 8/2003 | Patel et al. |
| 2003/0158518 A1 | 8/2003 | Schonholz et al. |
| 2003/0158574 A1 | 8/2003 | Esch et al. |
| 2003/0158575 A1 | 8/2003 | Boylan et al. |
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171769 A1 | 9/2003 | Barbut |
| 2003/0171770 A1 | 9/2003 | Kusleika et al. |
| 2003/0171771 A1 | 9/2003 | Anderson et al. |
| 2003/0171772 A1 | 9/2003 | Amplatz |
| 2003/0171800 A1 | 9/2003 | Bicek et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0717769 | 9/2003 | Barbut |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212431 A1 | 11/2003 | Brady et al. |
| 2003/0212432 A1 | 11/2003 | Khairkhahan et al. |
| 2003/0212433 A1 | 11/2003 | Ambrisco et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0220667 A1 | 11/2003 | van der Burg et al. |
| 2003/0225418 A1 | 12/2003 | Esksuri et al. |
| 2003/0225435 A1 | 12/2003 | Hunter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006365 A1 | 1/2004 | Brady et al. |
| 2004/0006370 A1 | 1/2004 | Tsugita |
| 2004/0015152 A1 | 1/2004 | Day |
| 2004/0039412 A1 | 2/2004 | Isshiki et al. |
| 2004/0049226 A1 | 3/2004 | Keegan et al. |
| 2004/0054394 A1 | 3/2004 | Lee |
| 2004/0054395 A1 | 3/2004 | Lee et al. |
| 2004/0059372 A1 | 3/2004 | Tsugita |
| 2004/0064067 A1 | 4/2004 | Ward |
| 2004/0064179 A1 | 4/2004 | Linder et al. |
| 2004/0068271 A1 | 4/2004 | McAlister |

(56) References Cited

U.S. PATENT DOCUMENTS

| | | |
|---|---|---|
| 2004/0078044 A1 | 4/2004 | Kear et al. |
| 2004/0082962 A1 | 4/2004 | Demarais et al. |
| 2004/0088038 A1 | 5/2004 | Dehnad et al. |
| 2004/0093009 A1 | 5/2004 | Denison et al. |
| 2004/0093012 A1 | 5/2004 | Cully et al. |
| 2004/0093016 A1 | 5/2004 | Root et al. |
| 2004/0093059 A1 | 5/2004 | Lee et al. |
| 2004/0098022 A1 | 5/2004 | Barone |
| 2004/0098026 A1 | 5/2004 | Joergensen et al. |
| 2004/0098033 A1 | 5/2004 | Leeflang et al. |
| 2004/0098112 A1 | 5/2004 | DiMatteo et al. |
| 2004/0102719 A1 | 5/2004 | Keith et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0138696 A1 | 7/2004 | Drasler et al. |
| 2004/0153118 A1 | 8/2004 | Clubb et al. |
| 2004/0158278 A1 | 8/2004 | Becker et al. |
| 2004/0162576 A1 | 8/2004 | Barbut et al. |
| 2004/0164030 A1 | 8/2004 | Lowe et al. |
| 2004/0167567 A1 | 8/2004 | Cano et al. |
| 2004/0176794 A1 | 9/2004 | Khosravi |
| 2004/0176833 A1 | 9/2004 | Pavcnik et al. |
| 2004/0199203 A1 | 10/2004 | Oslund et al. |
| 2004/0204737 A1 | 10/2004 | Boismier et al. |
| 2004/0215322 A1 | 10/2004 | Kerr |
| 2004/0225321 A1 | 11/2004 | Krolik et al. |
| 2004/0236369 A1 | 11/2004 | Dubrul |
| 2005/0004663 A1 | 1/2005 | Llanos et al. |
| 2005/0021125 A1 | 1/2005 | Stack et al. |
| 2005/0027345 A1 | 2/2005 | Horan et al. |
| 2005/0038468 A1 | 2/2005 | Panetta et al. |
| 2005/0038503 A1 | 2/2005 | Greenhalgh |
| 2005/0043743 A1 | 2/2005 | Dennis |
| 2005/0043756 A1 | 2/2005 | Lavelle et al. |
| 2005/0043780 A1 | 2/2005 | Gifford et al. |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009798 A1 | 1/2006 | Callister et al. |
| 2006/0009799 A1 | 1/2006 | Kleshinski et al. |
| 2006/0020334 A1 | 1/2006 | Lashinski et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0161241 A1 | 7/2006 | Barbut et al. |
| 2006/0184194 A1 | 8/2006 | Pal et al. |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287668 A1 | 12/2006 | Fawzi et al. |
| 2007/0038241 A1 | 2/2007 | Pal |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0149996 A1 | 6/2007 | Coughlin |
| 2007/0167974 A1 | 7/2007 | Cully et al. |
| 2007/0185521 A1 | 8/2007 | Bui et al. |
| 2007/0250108 A1 | 10/2007 | Boyle et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0103522 A1 | 5/2008 | Steingisser et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1310219 A2 | 5/2003 |
| EP | 1516601 | 3/2005 |
| EP | 1557137 A1 | 7/2005 |
| WO | WO 92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/82831 | 11/2001 |
| WO | WO 03/077799 A2 | 9/2003 |
| WO | WO 2006/138391 A2 | 12/2006 |

OTHER PUBLICATIONS

Heeschen et al., Nature Medicine 7 (2001), No. 7, pp. 833-839.
Johnson et al., Circulation Research 94 (2004), No. 2, pp. 262-268.
International Search Report and Written Opinion for PCT/US2007/020300.
Brochure, "Shuttle Select™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," *Modelling in Medicine and Biology IV*, (2005), vol. 8, pp. 133.
Grummon, David S. et al., Appl. Phys. Lett., 82, 2727 (2003), pp. 2727.

* cited by examiner

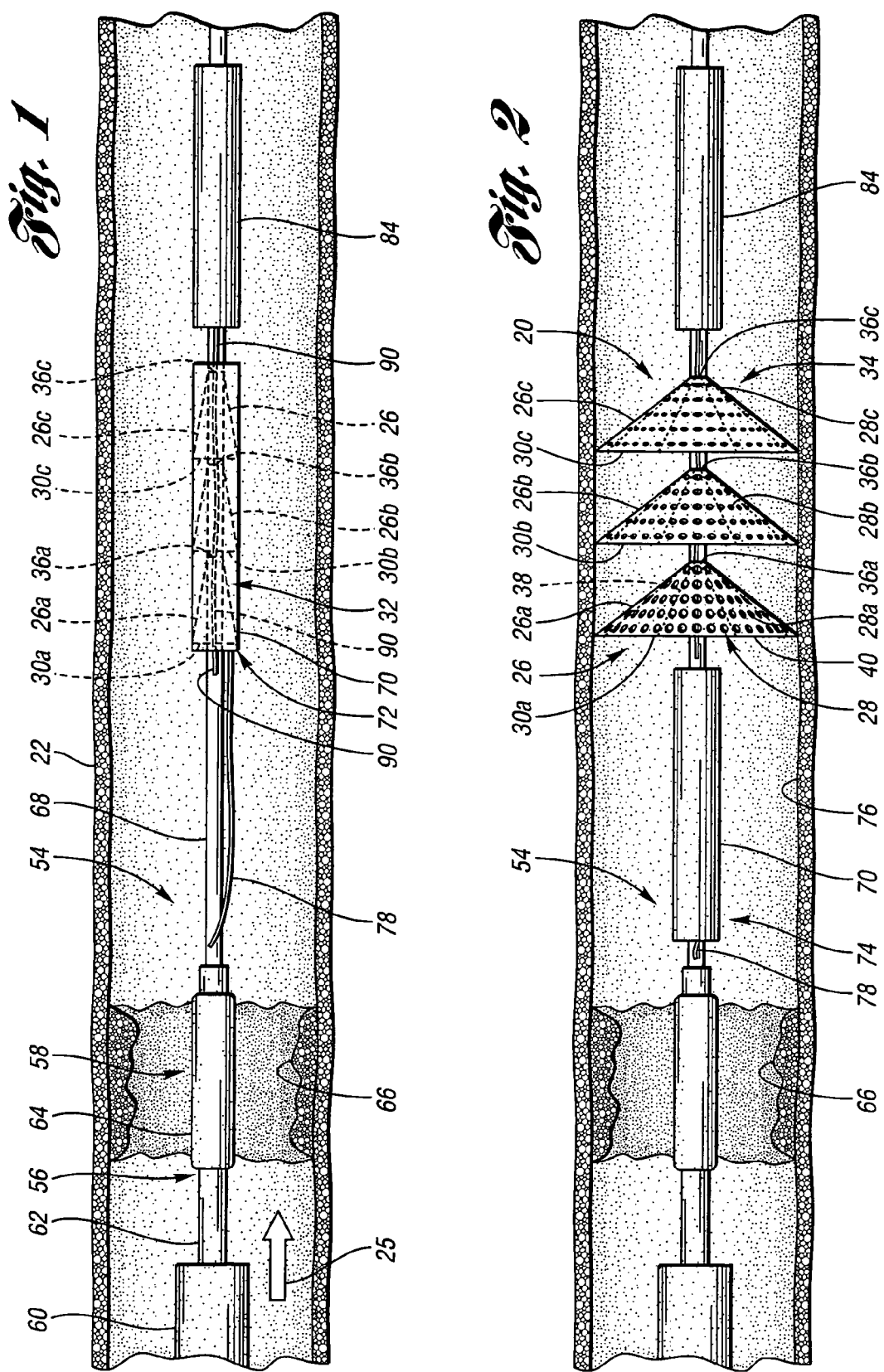

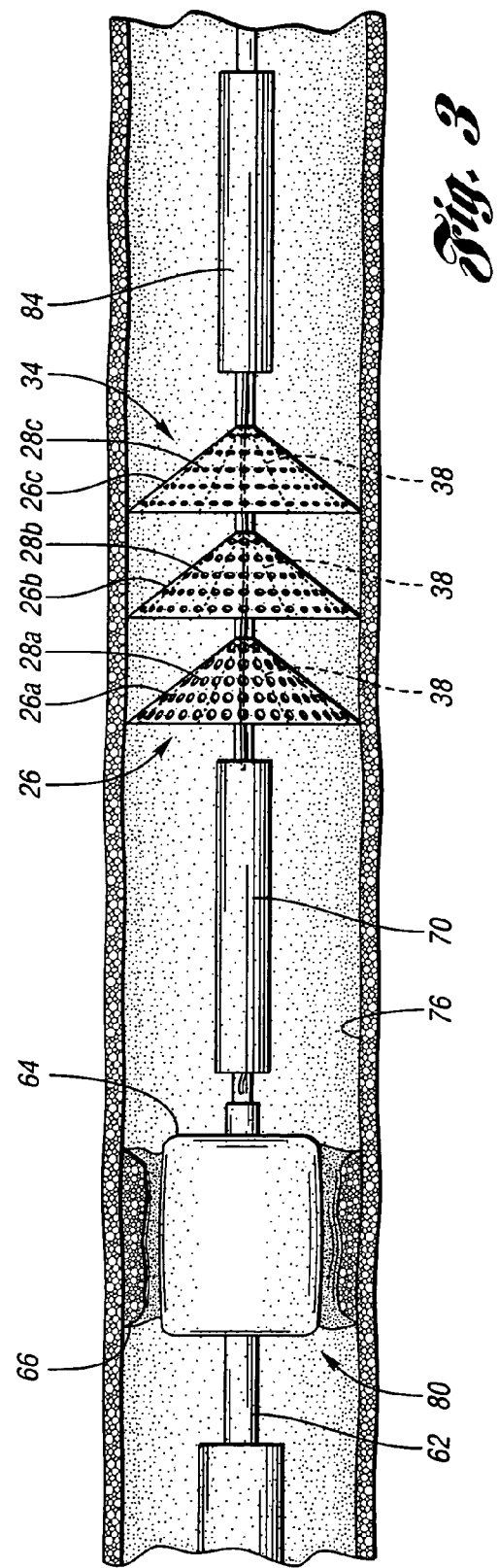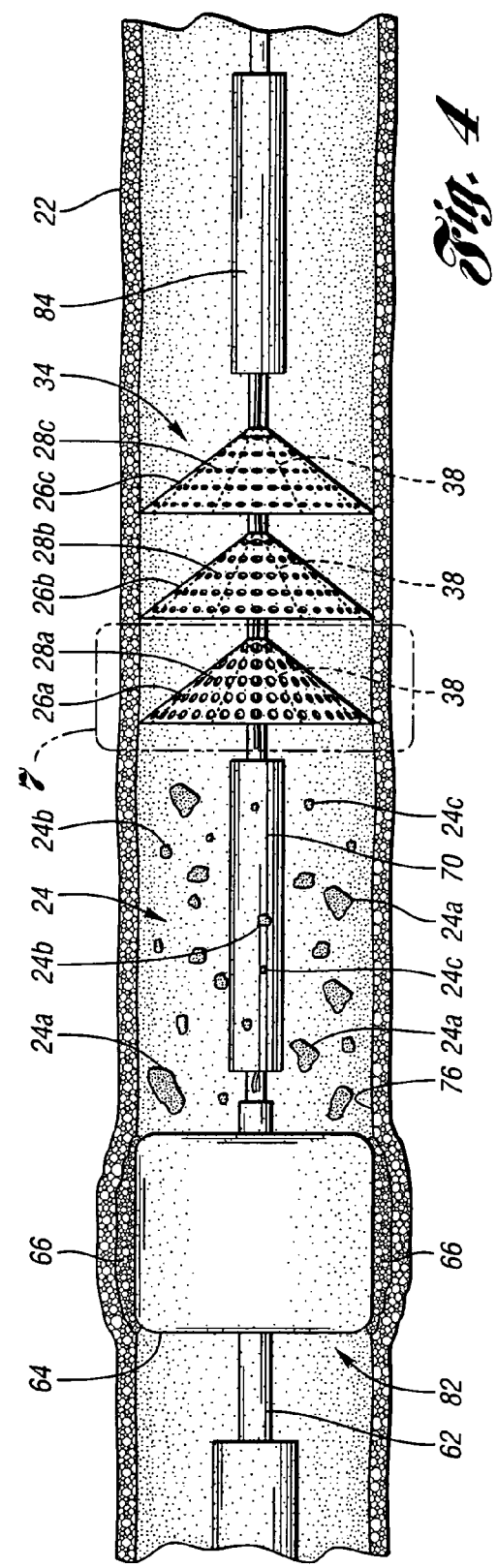

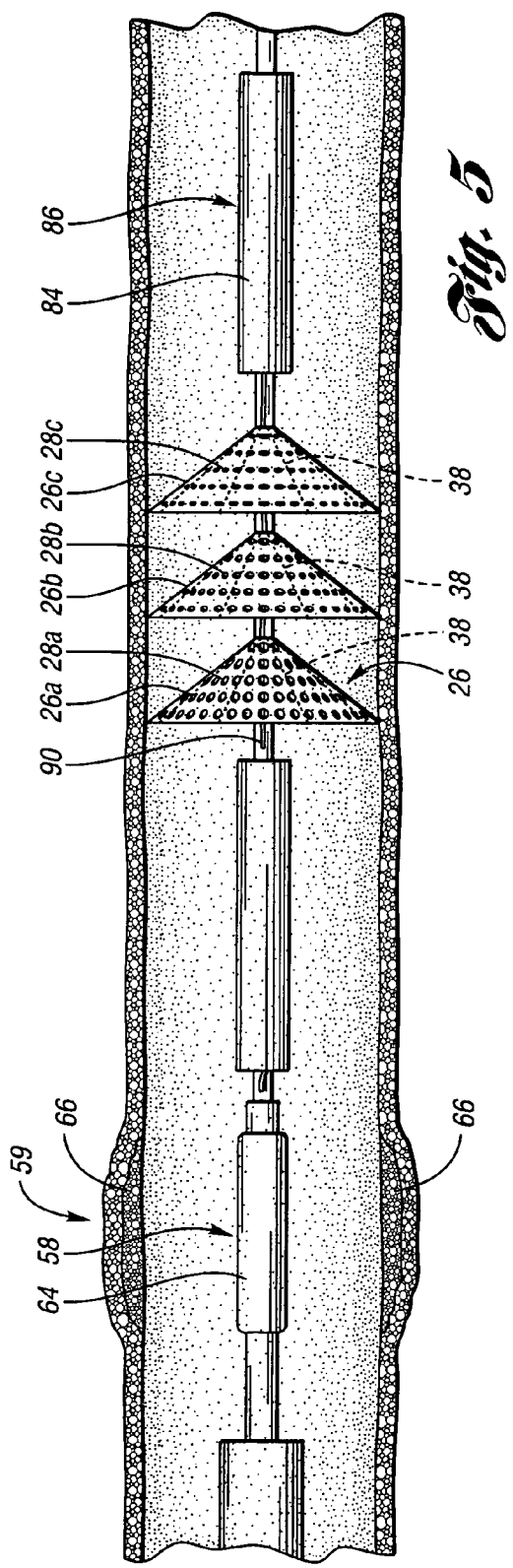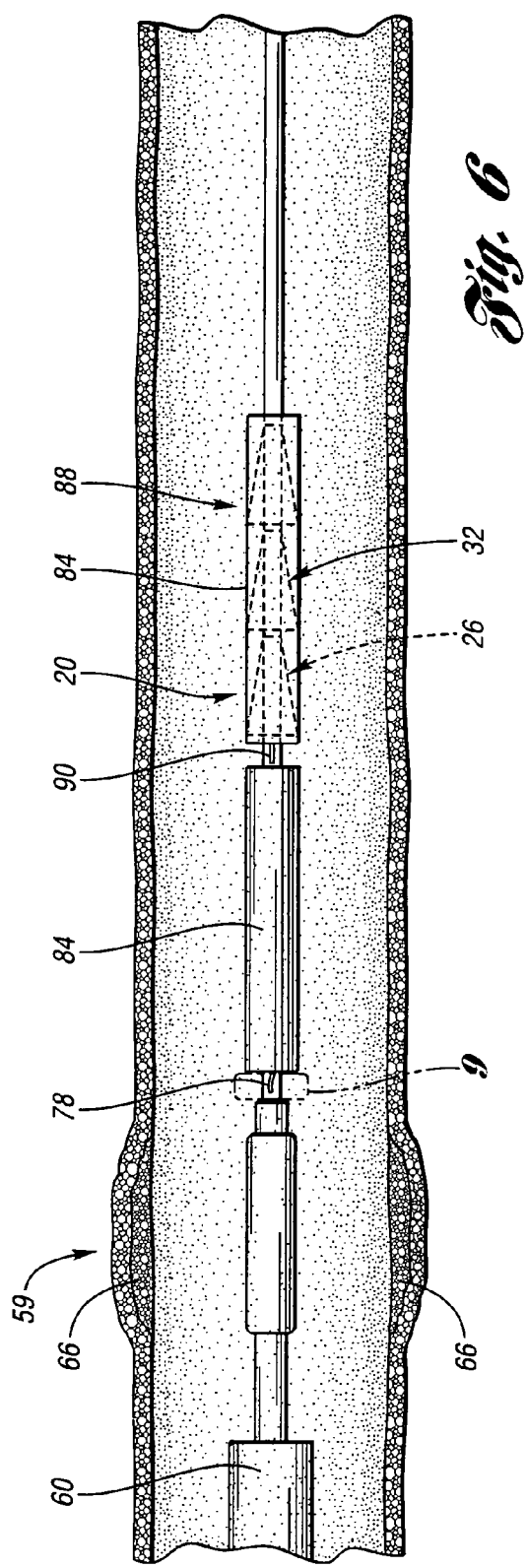

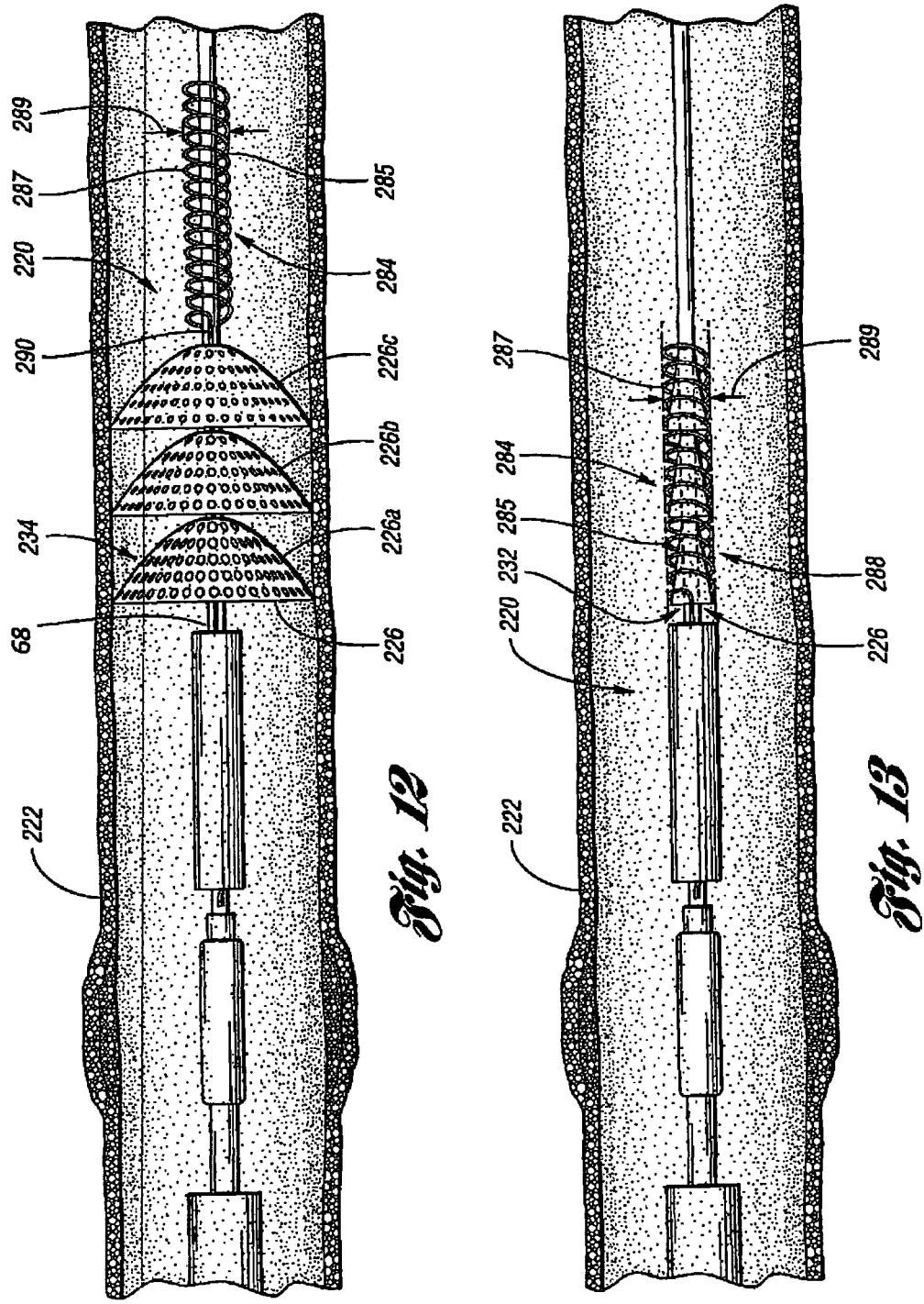

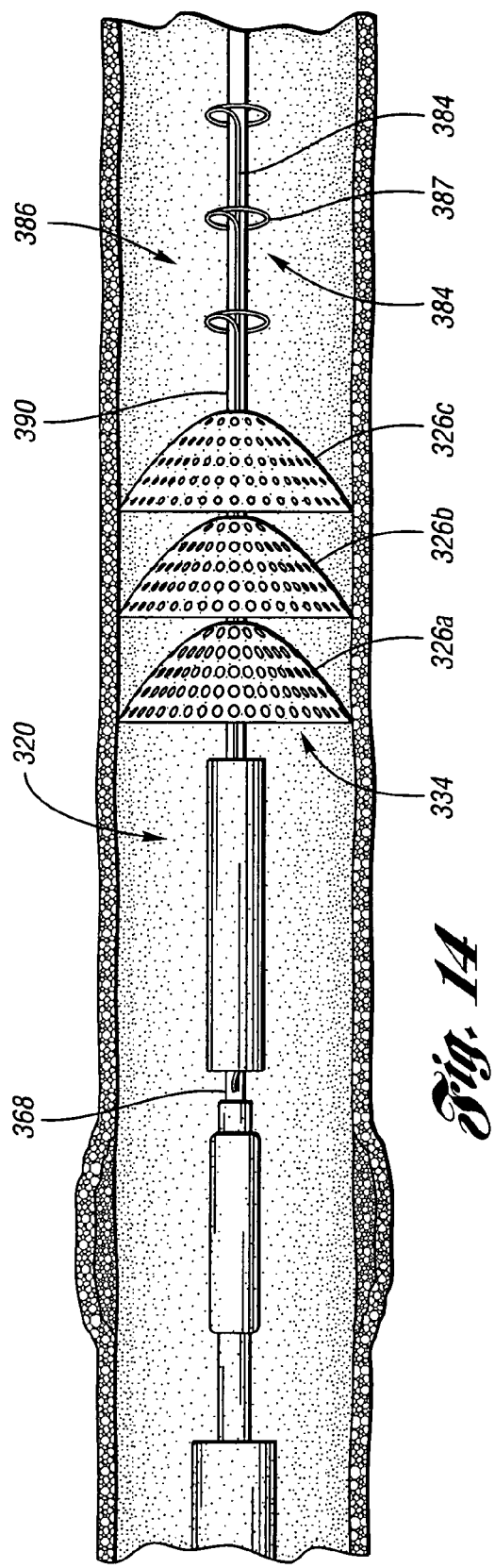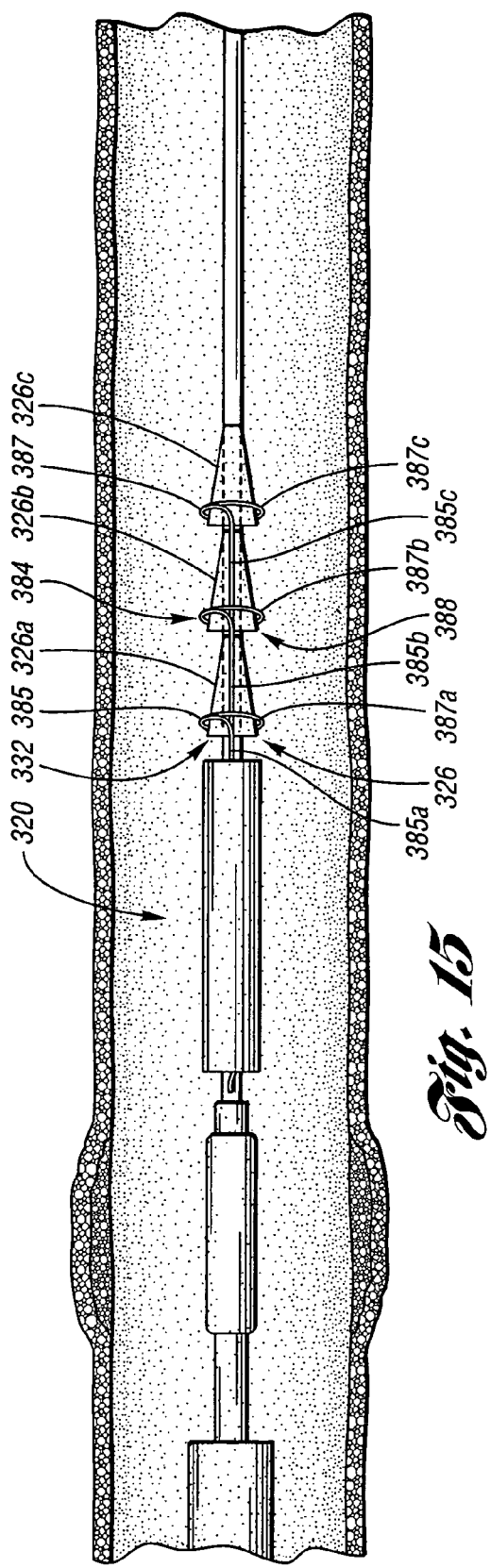

EMBOLIC PROTECTION DEVICE

CROSS-REFERENCE TO RELATED APPLICATION

This patent application claims the benefit under 35 U.S.C. §119(e) of U.S. provisional patent application Ser. No. 60/723,255, filed Oct. 3, 2005 and entitled EMBOLIC PROTECTION DEVICE, the entire contents of which are incorporated herein by reference.

BACKGROUND

1. Field of the Invention

The invention relates generally to medical devices. More specifically, the invention relates to intravascular embolic protection devices.

2. Related Technology

Embolic protection devices are percutaneously placed in a body vessel to prevent emboli from traveling and creating an undesirable embolism, e.g., pulmonary embolism. For example, vena cava filters are being used for trapping emboli in the vena cava filter to prevent pulmonary embolism. Also, anti-platelet agents and anticoagulants may be used to breakdown blood clots. Moreover, snares and baskets (e.g., stone retrieval baskets) are being used for retrieving urinary calculi. Additionally, occlusion coils are commonly used to occlude aneurysms and accumulate thrombi in a body vessel.

Treatments for a stenotic lesion provide a potential in releasing blood clots and other thrombi plaque in the vasculature of the patient. One example is the treatment for a carotid artery stenosis. Generally, carotid artery stenosis is the narrowing of the carotid arteries, the main arteries in the neck that supply blood to the brain. Carotid artery stenosis (also called carotid artery disease) is a relatively high risk factor for ischemic stroke. The narrowing is usually caused by plaque build-up in the carotid artery.

Carotid angioplasty is a more recently developed treatment for carotid artery stenosis. This treatment uses balloons and/or stents to open a narrowed portion of an artery. Carotid angioplasty is a procedure that can be performed via a standard percutaneous transfemoral approach with the patient anesthetized using light intravenous sedation. At the stenosis area, an angioplasty balloon is delivered to predilate the stenosis in preparation for stent placement. The balloon is then removed and exchanged via catheter for a stent delivery device. Once in position, a stent is deployed across the stenotic area. If needed, an additional balloon can be placed inside the deployed stent for post-dilation to make sure the struts of the stent are pressed firmly against the inner surface of the vessel wall. During the stenosis procedure however, such as during the predilation or during the stent delivery, there is a risk of such blood clots and thrombi being undesirably released into the blood flow within the vasculature.

Therefore, embolic protection devices, such as occlusive devices and filters, have been developed to trap and to prevent the downstream travel of the blood clots and thrombi. The filters are typically advanced downstream of a site that is to be treated and then expanded into an opened state to increase the filter area. The blood clots and thrombi can be captured in the opened filter while blood is still able to flow therethrough.

Once the stenosis procedure has been completed, the stent delivery device is removed from the stenotic area and is possibly removed completely from the body vessel. Next, after the blood clots and thrombi displaced by the angioplasty have been captured in the opened filter, the embolic protection device is removed from the body vessel. However, to prevent the captured blood clots and thrombi from being released back into the blood stream, the embolic protection device preferably includes a mechanism for securing the blood clots and thrombi during removal of the embolic protection device. Furthermore, to facilitate the removal of the embolic protection device and to minimize or prevent additional blood clots and thrombi from being released from the stenotic area, the embolic protection device preferably has a relatively small cross-sectional area during the removal thereof.

However, currently known filter devices may fail to completely secure the blood clots and thrombi during removal of the embolic protection device. As another drawback, currently known filter devices may not sufficiently radially collapse the filter device before or during extraction from the body vessel. Additionally, or alternatively, currently known filter devices may require relatively bulky components to employ or control the mechanism for securing the blood clots and thrombi.

Thus, there is a need to improve the cross-sectional size of the embolic protection device during extraction from the body vessel and a need to improve the mechanism for securing the blood clots and thrombi during the extraction.

SUMMARY

In one aspect of the present invention, an embolic protection device for deployment in a body vessel is provided for filtering emboli within the body vessel. The embolic protection device generally includes a filter having a plurality of openings formed therethrough and an extraction element configured to be movable with respect to the filter between a non-extraction position and an extraction position. The extraction element is located distally from the filter when in the non-extraction position so as to allow the filter to open into an expanded state to collect the emboli. Additionally, the extraction element is disposed about at least a portion of the filter when in the extraction position so as to close the filter into a collapsed state, to secure the collected emboli, and to permit the embolic protection device to be extracted from the body vessel.

In another aspect of the invention, the extraction element is an extraction sleeve. As an alternative design, the extraction element includes an extraction wire defining a loop. The extraction wire also may define a plurality of closed loops that are movable with respect to each other. In yet another alternative design, the extraction wire defines a coiled wire.

In yet another aspect, the filter includes a first filter element and a second filter element spaced apart from each other. Additionally, the first filter element defines a plurality of first filter openings and the second filter element defines a plurality of second filter openings, where the first filter openings are each larger than the second filter openings. The filter may also include a third filter element spaced apart from the first and the second filter elements.

In another aspect, the first filter openings decrease in size between a proximal portion and a distal portion of the first filter element and the second filter openings decrease in size between a proximal portion and a distal portion of the second filter element. This configuration promotes a complete self-expansion of each of the filter elements within the body vessel.

In yet another aspect of the present invention, the embolic protection device includes a delivery element that is movable with respect to the filter between a delivery position and a non-delivery position. The delivery element is disposed about at least a portion of the filter when in the delivery position so that the filter is in a collapsed state for delivery of the embolic protection device within the body vessel. Additionally, the delivery element is located proximally from the filter when in the non-delivery position so as to allow the filter to open into an expanded state and facilitate collection of the emboli.

The embolic protection device may also include: a filter control wire coupled with the filter to control the position thereof, an extraction control wire coupled with the extraction element to control the position thereof, and a delivery control wire coupled with the delivery element and to control the position thereof. In one design, the filter control wire is a hollow wire defining a conduit that receives at least a portion of the extraction control wire and at least a portion of the delivery control wire. Additionally, the outer diameter of the filter control wire is preferably substantially greater than each of the outer diameters of the extraction control wire and the delivery control wire.

In another aspect of the present invention, an assembly for removing emboli from a body vessel is provided. The assembly generally includes an inflatable catheter having an expanded state for expanding narrowed or restricted portions of the body vessel, an outer catheter for delivering the inflatable catheter into the body vessel, and an embolic protection device positioned distally of the inflatable catheter for collecting emboli that are potentially dislodged during expansion of the body vessel.

In another aspect of the present invention, an embolic protection device includes a first filter element and a second filter element, each having a proximal end and a distal end. The proximal end of the second filter element is connected to an outer surface of the first filter element to stabilize the filter elements and to prevent emboli from flowing around the embolic protection device.

The first filter element and the second filter element preferably overlap each other to define an overlapping distance along the longitudinal axis of the embolic protection device. Additionally, or alternatively, the embolic protection device includes a third filter element having a proximal end and a distal end, wherein the proximal end of the third filter element is connected to an outer surface of the second filter element. The three filter elements cooperate to define a substantially constant outer diameter between the proximal end of the first filter element and the distal end of the third filter element.

The second plurality of openings are generally smaller than the first plurality of openings and the third plurality of openings are generally smaller than the second plurality of openings so that the first filter element collects relatively large emboli, the second filter element collects medium-sized emboli, and the third filter element collects relatively small emboli.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 1 is an environmental side view of an embolic protection device in a collapsed state for delivery within a blood vessel in accordance with one embodiment of the present invention;

FIG. 2 is an environmental side view of the embolic protection device in FIG. 1 shown in an expanded state;

FIG. 3 is an environmental side view of the embolic protection device in FIG. 2 shown in conjunction with an inflatable catheter in a partially-expanded state so as to contact a stenotic lesion;

FIG. 4 is an environmental side view of the embolic protection device in FIG. 3 with the inflatable catheter in a completely expanded state, potentially dislodging emboli from the stenotic lesion;

FIG. 5 is an environmental side view of the embolic protection device in FIG. 4 with the inflatable catheter in a deflated state for extraction from the blood vessel;

FIG. 6 is an environmental side view of the embolic protection device in FIG. 5 in the collapsed state for extraction from the blood vessel;

FIG. 12 is an environmental side view of an alternative embolic protection device in an expanded state for collecting emboli from the blood stream in accordance with one embodiment of the present invention;

FIG. 13 is an environmental side view of the embolic protection device from FIG. 12 in a collapsed state for extraction from the blood vessel;

FIG. 14 is an environmental side view of yet another alternative embolic protection device in an expanded state for collecting emboli from the blood stream in accordance with one embodiment of the present invention;

FIG. 15 is an environmental side view of the embolic protection device from FIG. 14 in a collapsed state for extraction from the blood vessel;

DETAILED DESCRIPTION

Figure 8:
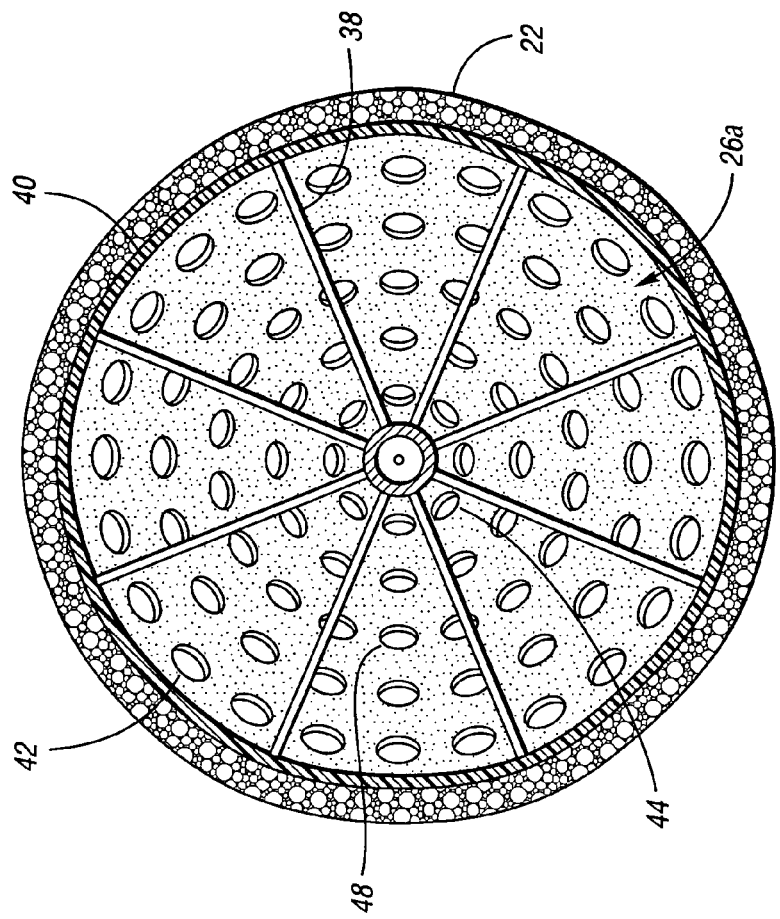
FIG. 8 is a cross-sectional view of the embolic protection device taken along line 8-8 in FIG. 7.

Embodiments of the present invention generally provide embolic protection devices, embolic protection apparatus, and methods for capturing emboli in a body vessel during angioplasty for treatment of a stenosis. One particular stenosis is a carotid artery stenosis. The embodiments reduce the concerns of current stenosis treatments, such as the relatively high risks of surgery and the potential release of emboli into the vasculature during the stenosis procedure. For example, embodiments of the present invention provide a relatively low risk approach to capturing emboli released during a stenosis procedure, e.g., balloon angioplasty.

Referring now to the drawings, FIGS. 1-6 show an embolic protection device 20 to be positioned within a body vessel, such as a blood vessel 22, for filtering emboli 24 (FIG. 4) from a blood stream 25. More specifically, the embolic device 20 includes a filter 26 positioned downstream of emboli 24, such as blood clots and plaque fragments, to trap and prevent the downstream travel of the emboli 24 and reduce the likelihood of downstream blood vessels becoming blocked. As will be discussed in more detail below, the filter 26 includes a plurality of openings 28 that permit blood to flow therethrough and that prevent the emboli 24 from doing the same. As will also be discussed in more detail below, the filter 26 preferably includes three filter elements 26a, 26b, 26c spaced apart from each other in series.

The filter elements 26a, 26b, 26c each preferably include an open, proximally-located lip portion 30a, 30b, 30c that selectively expands to receive the emboli 24 and a closed, distally-located base portion 36a, 36b, 36c to collect and/or store the emboli 24. The lip portion 30a, 30b, 30c is movable so that the embolic protection device 20 defines a collapsed state 32 (FIGS. 1 & 6) and an expanded state 34 (FIGS. 2 through 5). The expanded state 34 filter 26 is able to collect and trap emboli 24 within the respective filter elements 26a, 26b, 26c, while the collapsed state 32 filter 26 is able to be inserted and withdrawn from the blood vessel 22, as will be discussed in more detail below.

The filter 26, when in the expanded state 34, preferably has a generally decreasing radius such that a first cross-sectional area of the filter 26 taken along a plane adjacent to the lip portion 30 is substantially larger than a second cross-sectional area of the filter 26 taken along a second plane adjacent to the base portion 36. For example, the expanded state 34 filter 26 is preferably generally cone-shaped such as to have a constantly decreasing radius along a longitudinal axis. In the design shown in the figures, each of the individual filter elements 26a, 26b, 26c is generally cone-shaped.

The filter 26 may be made of any suitable filter material to be used for capturing emboli 24 from the stenotic lesion during treatment thereof. In one embodiment, the filter 26 is coated with or made of reconstituted or naturally-derived collagenous materials. Such materials that are at least bioresorbable will provide advantage in the present invention, with materials that are bioremodelable and promote cellular invasion and ingrowth providing particular advantage.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic—such as cefazolin), or during or after engraftment of the material in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

In this embodiment, the submucosa or other ECM material is used to temporarily adhere the filter 26 to the walls of a body vessel in which the embolic protection device 20 is deployed. As discussed above, the submucosa or other ECM material has a natural adherence or wettability to body fluids and connective cells comprising the connective tissue of a body vessel wall. Due to the temporary nature of the duration in which the embolic protection device 20 is deployed in the body vessel, host cells of the wall will adhere to the filter 26 but not differentiate, allowing for retrieval of the embolic protection device 20 from the blood vessel 22.

In other embodiments, the filter 26 may also or alternatively be made of a mesh/net cloth, nylon, polymeric material, Teflon, or woven mixtures thereof without falling beyond the scope or spirit of the present invention.

Each of the filter elements 26a, 26b, 26c also preferably includes a plurality of struts 38 (FIGS. 2-5 and 7) for supporting the filter material. For example, the struts 38 extend from the base portion 36 to the lip portion 30 of each of the filter elements 26a, 26b, 26c and are generally circumferentially evenly-spaced from each other at the lip portion 30. Additionally, the struts 38 are secured to an inner surface of the filter material such that the filter material and the struts 38 collapse and expand in unison.

The struts 38 may be comprised of any suitable material such as a superelastic material, stainless steel wire, cobalt-chromium-nickel-molybdenum-iron alloy, or cobalt-chrome alloy. It is understood that the struts 38 may be formed of any other suitable material, such as shape memory alloys. Shape memory alloys have the desirable property of returning to a remembered state when heated above a transition temperature. A shape memory alloy suitable for the present invention is a mixture of Nickel and Titanium available under the more commonly known name Nitinol. When this material is heated above the transition temperature, the material undergoes a phase transformation from martensite to austenic, such that material returns to its remembered state. The transition temperature is dependent on the relative proportions of the alloying elements Nickel and Titanium and the optional inclusion of alloying additives.

In one embodiment, the struts 38 are made from Nitinol with a transition temperature that is slightly below normal body temperature of humans, which is about 98.6 degrees Fahrenheit. Therefore, when the filter 26 is deployed in the blood vessel 22 and exposed to normal body temperature, the alloy of the struts 38 will transform to austenite, that is, the remembered state, which for one embodiment of the present invention is the expanded configuration when the filter 26 is deployed in the blood vessel 22, as will be discussed in more detail below.

Each of the filter elements 26a, 26b, 26c also preferably includes a frame 40 positioned at or adjacent to the lip portion 30a, 30b, 30c to form a substantially fluid-tight seal with the blood vessel 22. More specifically, when the filter 26 is in the expanded state 34, the frame 40 defines a generally circular shape so as to generally conform to the shape the blood vessel 22. The seal substantially prevents emboli 24 from flowing around the filter 26 and causing the above-described conditions.

However, the frame 40 is also preferably able to be radially collapsed when the filter 26 is in the collapsed state 32. For example, the frame 40 may include a plurality of flexible, telescoping portions so that the frame 40 remains a generally circular component with an adjustable radius, whether the frame 40 is in the collapsed state 32 or the expanded state 34. This design may be particularly advantageous because it allows the embolic protection device 20 to be used in blood vessels 22 of varying size while still retaining a generally circular shape. Alternatively, the frame 40 may include a plurality of generally rigid portions that are hingedly connected with each other so that the frame 40 is generally circular when in the expanded state 34 and is non-circular, such as a star shape, when the frame 26 is in the collapsed state 32. As yet another alternative design, the frame 40 may be a single component with a plurality of weakened portions to permit the frame 40 to collapse into a non-circular shape, such as a star shape, when the frame 26 is in the collapsed state 32.

In another alternative design, the filter 26 does not include a frame, and the struts 38 provide sole structural support for the filter material. This design may be particularly advantageous because it allows the embolic protection device 20 to be used in blood vessels 22 having varying sizes. In yet another alternative design, the filter 26 does not include a frame or struts, and the filter material is not structurally supported by any additional components. In this design, and preferably in the other designs described herein, the filter material is naturally expanded into the expanded state 34 by forces from the blood stream 25 flowing through the blood vessel 22.

The openings 28 defined by the filter elements 26a, 26b, 26c are preferably configured such as to effectively harness the blood stream 25 and to promote the natural expansion of filter 26. For example, referring to FIGS. 7 and 8, each of the filter elements 26a, 26b, 26c preferably includes proximal openings 42 that have a generally larger cross-sectional area than distal openings 44 to maximize the occluding capacity of the filter 26 and to promote full expansion of filter elements 26a, 26b, 26c within the blood vessel 22, as is discussed in more detail below.

Regarding the base portion 36, the distal openings 44 are relatively small so as to cause a flow resistance that is sufficient to open the filter 26. More specifically, the distal openings 44 are sized and positioned with respect to each other such that the filter 26 provides a flow resistance when the base portion 36 is folded. Therefore, when the filter 26 is in the collapsed state 32, such as when being initially deployed into the blood vessel 22, the filter 26 may become folded along creases such that some of the openings 28 become blocked. Therefore, the distal openings 44 are sized and positioned with respect to each other such as to provide a flow resistance unless substantially all of the distal openings 44 are unobstructed, thereby causing the filter 26 to naturally expand.

However, the distal openings 44 are preferably not so small as to restrict blood flow there through when the base portion 36 is fully opened and unobstructed. As discussed above, restricted blood flow can cause various undesirable medical conditions. Therefore, the distal openings 44 are large enough such as to not reduce blood flow through the filter 26.

The distal openings 44 are preferably located along an end face 46 of the filter 26 that is substantially perpendicular to the direction of the blood stream 25. This configuration also causes the filter 26 to fully open because the openings along the end face 46 have a maximum effective area when positioned to be perpendicular to the blood stream 25. Therefore, the natural properties of fluid flow will cause the end face 46 to be perpendicular to the direction of the blood stream 25, thus opening the filter 26 to its full length and maximizing its trapping volume.

Regarding the lip portion 30, the proximal openings 42 are relatively large to act as overflow passages for the distal openings 44 if they become obstructed. As emboli 24 flow into the filter 26 and engage the base portion 36, the distal openings 44 may become obstructed, thereby limiting the fluid flow through the base portion 36. To compensate for this reduced flow are, the proximal openings 42 have relatively large cross-sections. Therefore, the large proximal openings 42 substantially prevent the embolic protection device 20 from causing flow loss.

Figure 7:
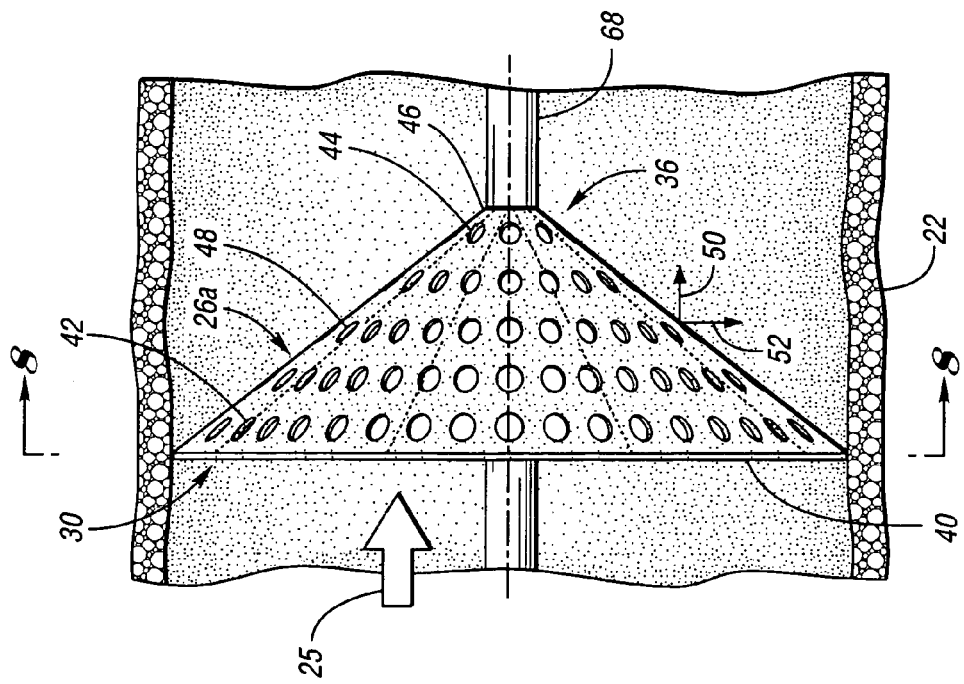
FIG. 7 is an enlarged portion of the embolic protection device indicated by line 7-7 in FIG. 4.

As shown in FIGS. 7 and 8, intermediate openings 48 are located axially between the proximal and distal openings 42, 44 such as to define flowpaths there through. The intermediate openings 48 are generally decreasing in size along the axial length in the direction of the blood stream 25. Furthermore, the proximal openings 42 are generally more spaced-apart from each other than the distal openings 44. Additionally, the intermediate openings 48 become generally less spaced-apart along the axial length of the respective filter elements 26a, 26b, 26c in the direction of the blood stream 25.

The proximal openings 42 may serve as continuously-used passages, such that blood continuously flows through the proximal openings 42, whether the distal openings 44 are obstructed or unobstructed. However, due to the generally cone-shaped nature of the filter elements 26a, 26b, 26c, the radially central portion of the filter receives the majority of the flow therethrough. More specifically, the natural fluid properties of the blood flow, such as friction between the blood flow and the blood vessel walls, cause the radially central portion of the blood vessel 22 to have a higher mass flow volume than the radially outer portion of the blood vessel 22. Furthermore, the tapered shape of the filter elements 26a, 26b, 26c directs blood towards the base portion 36 and thus towards the distal openings 44.

In addition to maximizing the trapping volume of and minimizing the flow losses through, the filter 26 also includes features that maximize the radial expansion of the embolic protection device 20. More specifically, to effectively form a seal between the filter 26 and the blood vessel 22 and thus prevent emboli 24 from flowing past the filter 26, the embolic protection device 20 is configured such that blood flow causes the filter 26 to be radially opened until it engages the blood vessel 22 inner walls.

One such feature that radially opens the filter 26 is the generally cone-shaped design of the filter 26. This shape causes blood flow along the direction of the blood stream 25 to create an axial force component 50 and a radial force component 52. More specifically, the axial force component 50 extends the filter 28 along its length, as discussed above. Furthermore, the radial force component 52 extends the filter 26 outwardly in the radial direction, towards the blood vessel 22 inner walls. Therefore, the cone-shaped nature of the filter 26 improves the seal and increases the trapping volume of the device 20.

In the embodiment shown in the figures, another such feature that radially opens the filter 26, or maintains the opened state thereof is the submucosa or other ECM material promoting biofixation between the filter 26 and the body vessel 12 discussed above. More specifically, the outer surface of the filter 26 includes a connective tissue that causes biofixation between the outer surface of the filter 26 and the inner surface of the blood vessel 22, thereby sealing the respective components 26, 22 together. The connective tissue is located on the frame 26 and on a portion of the filter 26 immediately adjacent to the lip portion 30. Additionally, the connective tissue may be located on the outer surface along a length of the filter 26 such as to increase the surface area of the seal. As another design, the connective tissue may be a coating along the entire length of the filter 26. As yet another design, the filter material may be completely formed of the connective tissue.

Referring back to FIGS. 1-6, the filter elements 26a, 26b, 26c are each respectively configured such as to collect emboli 24 of varying sizes and shapes. For example, the first filter element 26a defines a first set of openings 28a having a relatively large size so that only relatively large emboli 24a are collected by the first filter element 26a and smaller emboli are permitted to flow therethrough. Additionally, the second filter element 26b defines a second set of openings 28b having a medium size so that only medium-sized emboli 24b are collected by the second filter element 26b and smaller emboli are permitted to flow therethrough. Furthermore, the third filter element 26c defines a third set of openings 28c having a relatively small size so that the remaining, relatively small emboli 24c are collected by the third filter element 26c and blood cells are permitted to flow therethrough.

In one configuration, each of the openings 28a in the first filter element 26a is larger than each of the openings 28b in the second filter element 26b and each of the openings 28b in the second filter element 26b is larger than each of the openings 28c in the third filter element 26c. In another configuration, the proximal openings in the in the first filter element 26a are larger than the proximal openings in the second filter element 26b and the distal openings in the in the first filter element 26a are larger than the distal openings in the second filter element 26b, but the proximal openings in the first filter element 26a are not larger than the distal openings in the second filter element 26b. In other words, in this configuration, the average size of the openings decreases from the first filter element 26a to the third filter element 26c, but some of the openings in the second or third filter elements 26b, 26c may still be smaller than some of the openings in the first filter element 26a. Alternatively, any suitable configuration of the openings may be used.

The above-described configuration is beneficial for reducing the cross-sectional area of the filter 26 when the emboli 24 are trapped therewithin. In other words, each of the filter elements 26a, 26b, 26c is able to collect a generally equal amount of emboli 24, thereby equally distributing the emboli 24 among the filter elements 26a, 26b, 26c. This configuration is particularly beneficial for reducing the cross-sectional area of the filter 26 when in the collapsed state 32, as will be discussed in more detail below.

Although three filter elements 26a, 26b, 26c are shown in the figures, any suitable number of elements may be used with the present invention. For example, a single filter element may be employed in the embolic protection device 20.

Generally, during use, the device 20 is inserted into the blood vessel 22 while in the collapsed state 32. Additionally, the device 20 is then expanded from the collapsed state 32 to the expanded state 34 so that the filter 26 engages the blood vessel 22. As a result, the lip portion 30 of each of the respective filter elements 26a, 26b, 26c opens for capturing emboli during treatment of the stenotic lesion. After the need for such device 20 in the vasculature passes, the device 20 may be closed to the collapsed state 32 and retrieved.

To illustrate a more specific example, FIGS. 1-6 show an assembly 54 for treatment of a stenotic lesion 66. As shown in FIG. 1, the assembly 54 includes an inflatable catheter 56 in a deflated state 58 and an outer catheter 60 supporting and delivering the inflatable catheter 56 into the blood vessel 22. More specifically, the inflatable catheter 56 includes a tubular body 62 and an expandable balloon 64 attached to and in fluid communication with the tubular body 62 for an angioplasty at the stenotic lesion 66. In this embodiment, the assembly 54 includes the embolic protection device 20 described above. Furthermore, the assembly 54 also includes a filter control wire 68 for guiding the inflatable catheter 56 coupling the embolic protection device 20 thereto.

A method of utilizing the assembly 54 will now be discussed in more detail. First, as shown in FIG. 1, the filter control wire 68 is inserted percutaneously into the blood vessel 22 and advanced therealong, past the stenotic lesion 66. The filter control wire 68 may be advanced along an already-inserted wire guide (not shown) known in the art or may be advanced solely along the blood vessel 22. Next, the outer catheter 60 is percutaneously inserted into the blood vessel 22 and advanced along the filter control wire 68 until positioned at a desired location, which is preferably proximal of the stenotic lesion 66. The embolic protection device 20 is then advanced from the outer catheter 60 to a desired location, which is preferably distal of the stenotic lesion 66. At this point, the filter 26 is in the collapsed state 32, preferably due to the presence of a delivery sleeve 70 in a delivery position 72, as will be discussed in more detail below. Next, or simultaneously with the advancing of the embolic protection device 20, the assembly 54 is advanced to a desired location such that the expandable balloon 64, still in the deflated state 58, is aligned with the stenotic lesion 66.

Next, as shown in FIG. 2, the delivery sleeve 70 is moved from the delivery position 72 to a non-delivery position 74 that is between the stenotic lesion 66 and the filter 26 so that the filter elements 26a, 26b, 26c are able to expand into the expanded state 34, as discussed above. More specifically, each of the filter elements 26a, 26b, 26c expands to contact an inner wall 76 of the blood vessel 22 and form a generally fluid-tight seal therewith. The filter elements 26a, 26b, 26c preferably expand due to natural forces, such as the shape memory forces or the blood stream 25 forces discussed above.

The seal preferably prevents emboli 24 from flowing between the filter 26 and the blood vessel inner wall 76, thereby preventing or minimizing the above-described conditions. The delivery sleeve 70 is preferably moved with respect to the filter 26 via a delivery control wire 78 that is able to be retracted with respect to the filter control wire 68, as will be discussed in more detail below. Although the delivery sleeve 70 is shown as being positioned between the stenotic lesion 66 and the filter 26 when in the non-delivery position 74, any suitable non-delivery position may be used. For example, the delivery sleeve 70 may be retracted over the assembly 54 and completely removed from the blood vessel 22.

Next, the expandable balloon 64 is expanded into a partially-expanded state 80 (FIG. 3) so that it contacts the stenotic lesion 66 and is further expanded into an expanded state 82 (FIG. 4) so that it expands the body vessel 22 in the area of the stenotic lesion 66. As mentioned above, the expansion of the body vessel 22 potentially causes the release of emboli 24 into the blood stream, which are captured by the filter elements 26a, 26b, 26c. The expandable balloon 64 is preferably expanded by a fluid, such as water or saline solution, which is injected along the tubular body 62 into the expandable balloon 64. More specifically, the tubular body 62 preferably has a ring-shaped cross-section, not unlike a doughnut, so that the filter control wire 68 is able to travel through the central opening of the tubular body 62 and so that the fluid is able to travel along a conduit surrounding the filter control wire 68. At this point in the procedure, the filter 26 preferably remains in the expanded state 34, as shown in FIGS. 3 and 4, to collect the emboli 24.

Next, as shown in FIG. 5, the expandable balloon 64 is deflated back into the deflated state 58 by extracting the fluid therefrom via the tubular body 62. Although the expandable balloon 64 no longer contacts the stenosis 66 after the deflation of thereof, the body vessel 22 typically still defines a generally unobstructed flow path. More specifically, the body vessel 22 walls in the area of the stenosis 66 substantially remain in an expanded state 59 and the blood stream 25 is substantially unobstructed. While the expandable balloon 64 is being deflated the filter 26 preferably still remains in the expanded state 34, as shown in FIG. 5, to collect emboli 24 that may be released into the blood stream 25.

As shown in FIG. 6, the filter 26 is then collapsed into the collapsed state 32 by an extraction sleeve 84. For example, the extraction sleeve 84 is advanced from a non-extraction position 86 (FIGS. 1-5) to an extraction position 88 to radially compress the filter 26. When in the non-extraction position 86, the extraction sleeve 84 is located distally of the filter 26. Conversely, when in the retraction position 88, the extraction sleeve 84 is disposed about the filter 26.

As is known in the art, the term "proximal" refers to the portion of the embolic protection device 20 that is not positioned within the body vessel 22 during normal use of the embolic protection device 20 and the term "distal" refers to the opposing portion of the embolic protection device 20, which may be positioned within the body vessel 22. Therefore, when the extraction sleeve 84 is moved from the non-extraction position 86 to the extraction position 88, the device 20 is moved proximally. Similarly, when the embolic protection device 20 is extracted from the body vessel 22, it is likewise moved proximally. In this configuration, the filter 26 is collapsed into the extraction position 88 in the same direction as the direction of travel during extraction, thereby potentially reducing the likelihood that emboli escape from the filter 26 while the filter 26 is being collapsed.

The extraction sleeve 84 is preferably moved with respect to the filter 26 via an extraction control wire 90 that is able to be retracted with respect to the filter control wire 68, as will be discussed in more detail below.

When the filter 26 is in the collapsed state 32, the diameter is substantially reduced, thereby effectively securing the emboli 24 in the respective filters 26a, 26b, 26c and reducing the overall diameter of the embolic protection device 20 so that it can be retracted through the outer catheter 60. The assembly 54 discussed herein may be used with any other suitable procedure.

In the embodiment shown in FIGS. 1-6, both the delivery sleeve 70 and the extraction sleeve 84 are hollow tubes made of any suitable material, such as mesh/net cloth, nylon, polymeric material, Teflon, or a woven mixture of any of the above materials. The sleeves 70, 84 are preferably radially flexible enough so as to negotiate the winding paths of the blood vessel 22, but are preferably not radially flexible enough so that they substantially radially expand when disposed around the filter so as to fail to effectively secure the emboli 24. The sleeves 70, 84 shown in FIGS. 1-6 have equal diameters so that the filter 26 in the collapsed state 32 shown in FIG. 1 has the same diameter as the filter 26 in the collapsed state 32 shown in FIG. 6. However, the filter 26 may have different diameters during the respective stages of the procedure.

Figure 9:
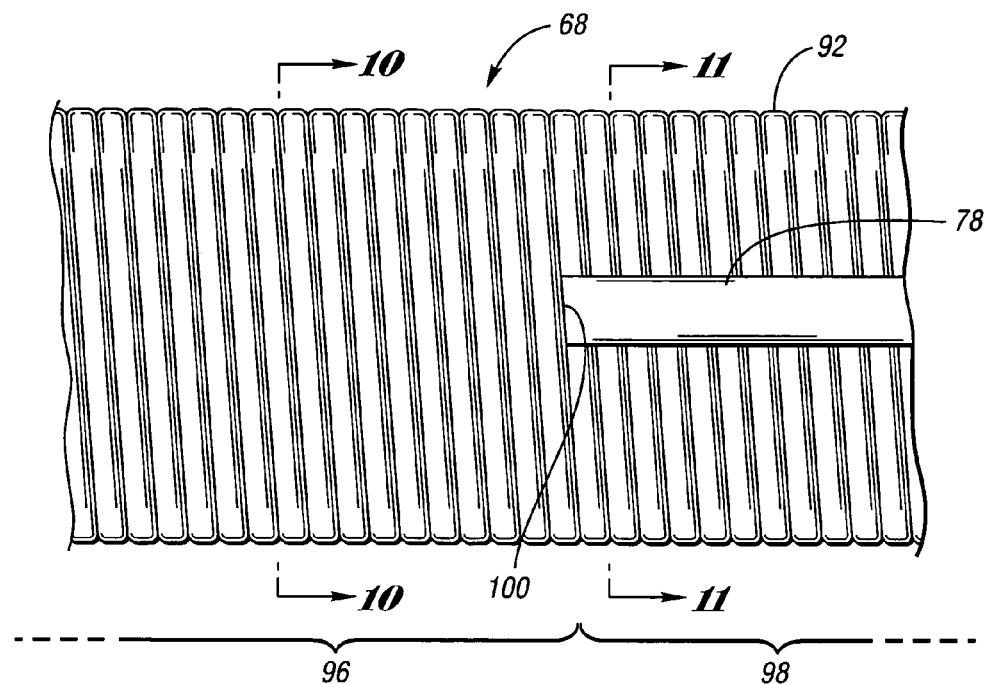
FIG. 9 is an enlarged portion of the embolic protection device indicated by line 9-9 in FIG. 6 showing a filter control wire and a delivery control wire.
Figures 10, 11:
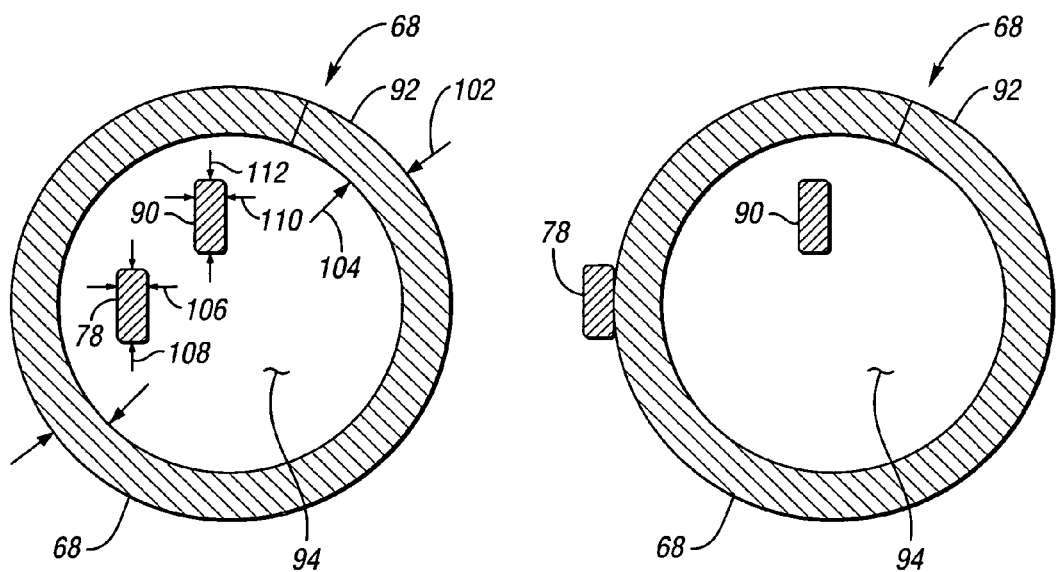
FIG. 10 is a cross-sectional view of the embolic protection device taken along line 10-10 in FIG. 9.
FIG. 11 is a cross-sectional view of the embolic protection device taken along line 11-11 in FIG. 9.

Referring to FIGS. 9-11, the configuration of the filter control wire 68, the delivery control wire 78, and the extraction control wire 90 will now be discussed in more detail. The filter control wire 68 shown in the figures is formed of a tightly-coiled wire 92 having an axial stiffness and a radial flexibility that are conducive to navigation of tortuous pathways of the blood vessel 22. The filter control wire 68 may be made of any suitable material or combination of materials that are biocompatible or capable of being made biocompatible, such as stainless steel, other biologically compatible metals, polymers, plastics, alloys (including super-elastic alloys), or composite materials. The filter control wire 68 in the figures is a single coiled wire 92 wound at a pitch angle suitable for a desired flexibility. A relatively steep pitch angle, which is defined as being generally close to 90 degrees, is typically more flexible than a generally shallow pitch angle. The pitch angle of the coiled wire 92 may vary along the length of the filter control wire 68 to affect the radial stiffness thereof. In an alternative design, the filter control wire 68 may be a multiple filament, helically wound row of wires, similar to that disclosed in the U.S. Patent Application entitled "ENDOVASCULAR MEDICAL DEVICE WITH PLURALITY OF WIRES" having Ser. No. 10/615,314, which was filed on Jul. 7, 2003 and which is incorporated herein by reference.

The coiled wire 92 defines a hollow conduit 94 extending along the filter control wire 68 and providing guidance for portions of the embolic protection device 20. For example, the delivery control wire 78 and the extraction control wire 90 extend at least partially along the conduit 94 for guidance through the blood vessel 22 and for space efficiency. More specifically, as shown in FIG. 9, the delivery control wire 78 is located within the conduit 94 along a first portion 96 of the filter control wire 68, is located outside of the conduit 94 along a second portion 98 of the filter control wire 68, and extends out of the conduit 94 at a transition point 100 between a pair of adjacent coil sections. The transition point 100 for the delivery control wire 78 is preferably located proximal to the non-delivery position 74 so that the delivery sleeve 70 may be easily retracted to the non-delivery position 74. Similarly, a transition point for the extraction control wire 90 is preferably located proximal to the non-extraction position 86 so that the extraction sleeve 84 may be easily retracted to the non-extraction position 86.

Because the delivery sleeve 70 and the extraction sleeve 84 are only moving in a proximal direction with respect to the filter 26 during the above-described treatment, the respective sleeves 70, 84 may be controlled by pulling on the respective control wires 78, 90 and/or pushing on the filter control wire 68. Therefore, because the respective control wires 78, 90 are only pulled and not pushed, they do not require a relatively high axial stiffness compared to the filter control wire 68 and thereby do not require a relatively high cross-sectional area compared to the filter control wire 68. This configuration is especially beneficial because the delivery control wire 78 and the extraction control wire 90 are more easily positioned within the conduit 94 to reduce the space of the embolic protection device 20.

In one example, referring to FIGS. 10 and 11, the filter control wire 68 has a generally circular cross-section with an outer diameter 102 of 0.13 inches and an inner diameter 104 of 0.06 inches. In this example, the delivery control wire 78 has a generally rectangular cross-section with a thickness 106 of 0.001 inches and a height 108 of 0.003 inches. Furthermore, the extraction control wire 90 has a generally rectangular cross-section with a thickness 110 of 0.001 inches and a height 112 of 0.003 inches. However, control wires 68, 78, 90 with any suitable dimensions and configurations may be used.

Referring now to FIG. 12, an alternative embodiment of the present invention is shown. In this embodiment, an embolic protection device 220 is shown with an extraction element 284 that is an extraction wire 285 defining a coil 287. As with the embolic protection device shown in FIGS. 1-6, the extraction element 284 is movable between a non-extraction position 286 (FIG. 12) and an extraction position 288 (FIG. 13). More specifically, when in the non-extraction position 286, the extraction wire 285 is spaced distally of the filter 226 so that the filter elements 226a, 226b, 226c are able to expand into an expanded state 234.

When in the extraction position 288, the extraction wire 285 is disposed about the filter 226 so that the filter elements 226a, 226b, 226c are compressed into a collapsed state 232 having a relatively small collapsed diameter 289 for extraction from the blood vessel 222. The extraction wire 285 is moved from the non-extraction position 286 to the extraction position 288 by an extraction control wire 290. For example, a physician is able to pull on the extraction control wire 290 while holding the filter control wire 68 steady. The embolic protection device 220 shown in FIGS. 12 and 13 is especially advantageous because the coil 287 can be stored in an axially compressed state when in the non-extraction position 286 to reduce the axial length of the embolic protection device 220.

Referring now to FIG. 14, another alternative embodiment of the present invention is shown. In this embodiment, an embolic protection device 320 is shown with an extraction element 384 that includes a plurality of extraction wires 385, each defining a single loop 387. As with the embolic protection device shown in FIGS. 12 and 13, the extraction element 384 is movable between a non-extraction position 386 (FIG. 14) and an extraction position 388 (FIG. 15). More specifically, when in the non-extraction position 386, the extraction wire 385 is spaced distally of the filter 326 so that the filter elements 326a, 326b, 326c are able to expand into an expanded state 334.

When in the extraction position 388, the extraction wire 385 is disposed about the filter 326 so that the filter elements 326a, 326b, 326c are compressed into a collapsed state 332 having a relatively small collapsed diameter 289 for extraction from the blood vessel 322. More specifically, the extraction wire 385 includes a single loop 387a that surrounds the first filter element 326a so that the first filter element 326a is compressed into a collapsed state 332 for extraction from the blood vessel 322. Similarly, two other extraction wires 385b, 385c define single loops 387b, 387c that surround the second and third filter elements 326b, 326c respectively so that the filter elements 326b, 326c are also compressed into the collapsed state 332. The three extraction wires 385a, 385b, 385c may be controlled by a single control wire so that they can be simultaneously deployed into the extraction position 388, or they can be independently controlled. This configuration is especially advantageous because the three loops 387a, 387b, 387c can be stored in an axially compressed state when in the non-extraction position 386 to reduce the axial length of the embolic protection device 320. The extraction wire 385 is moved from the non-extraction position 386 to the extraction position 388 by an extraction control wire 390. For example, a physician is able to pull on the extraction control wire 390 while holding the filter control wire 368 steady.

The extraction element 384 may alternatively be positioned such that, when in the non-extraction position 386, each of the three loops 387a, 387b, 387c is positioned immediately distally one of the filters 326a, 326b, 326c. More specifically, when in the non-extraction position 386, the first loop 387a is positioned between the first and second filters 326a, 326b; the second loop 387b is positioned between the second and third filters 326b, 326c; and the third loop 387c is positioned immediately distally of the third filter 326c.

Figure 16:
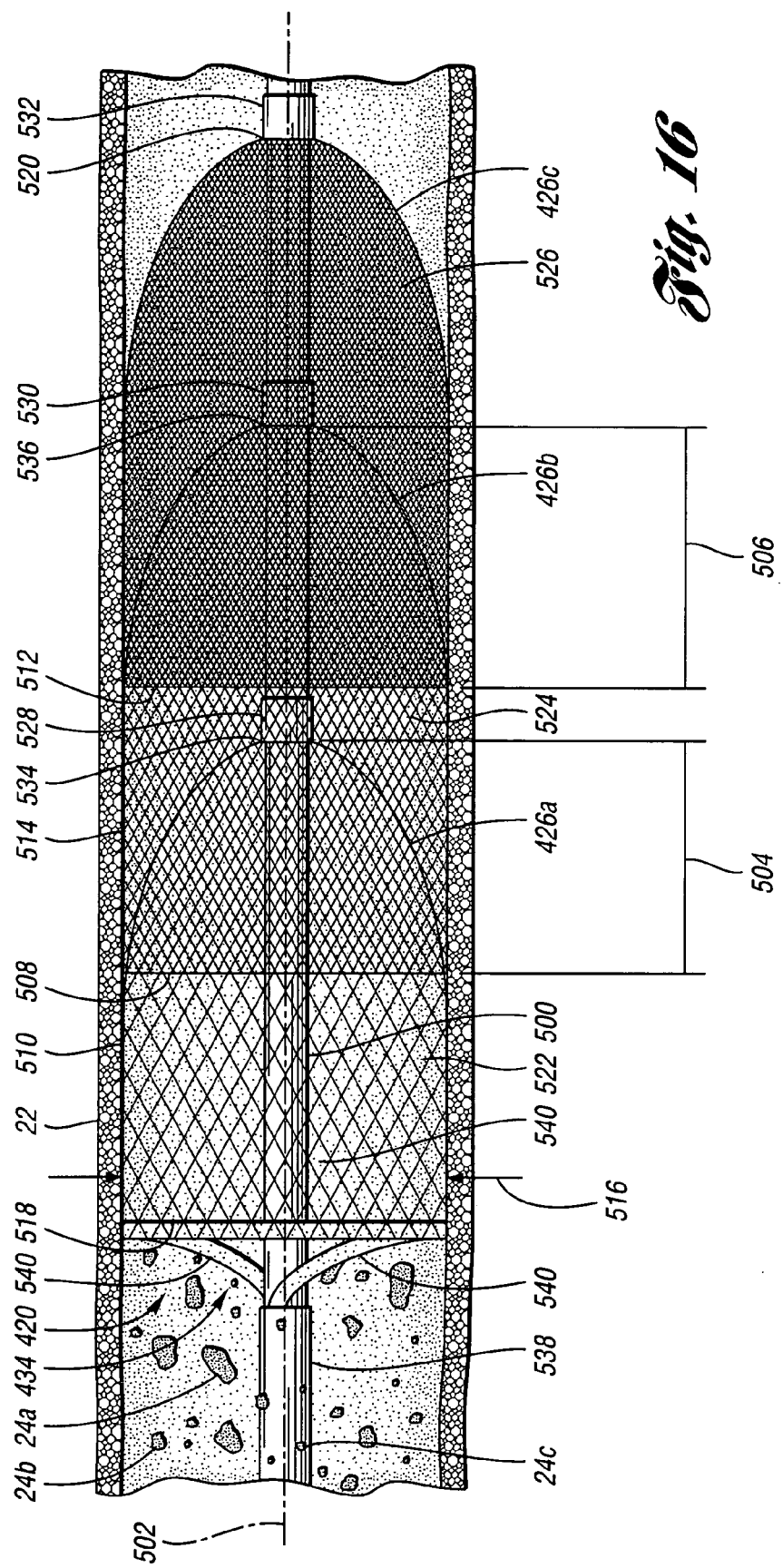
FIG. 16 is an environmental side view of another alternative embolic protection device in an expanded state in accordance with one embodiment of the present invention.

Referring now to FIG. 16, yet another alternative embodiment of the present invention is shown. In this embodiment, an embolic protection device 420 is shown in an expanded state having first, second, and third filter elements 426a, 426b, 426c positioned in tandem along a center core wire 500 that extends along a longitudinal axis 502. The filter elements 426a, 426b, 426c overlap each other along the longitudinal axis 502 so that the first and second filter elements 426a, 426b define an overlapping distance 504 and the second and third filter elements 426b, 426c define a second overlapping distance 506.

Furthermore, the respective filter elements 426a, 426b, 426c are preferably connected to each other to stabilize the embolic protection device 420 and to prevent emboli from flowing around the embolic protection device. More specifically, a proximal end 508 of the second filter element 426b is connected to an outer surface 510 of the first filter element 426a and a proximal end 512 of the third filter element 426c is connected to an outer surface 514 of the second filter element 426b. The emboli 24 that flow into the mouth portion of the embolic protection device 420 therefore remain within one of the filters element 426a, 426b, 426c even after flowing through an opening in the proximally-located filter element. In other words, the embolic protection device 420 shown in FIG. 16 needs only a single seal with the blood vessel 22—the seal at the proximal end 518 of the first filter element 426a—rather than three seals between the respective filter elements and the blood vessel 22. Furthermore, because the actual filter elements 426a, 426b, 426c are connected to each other, no additional sleeve is needed to surround the embolic protection device 420 to keep the emboli within a filter element at all times. The respective filter elements 426a, 426b, 426c are connected with each other by any appropriate means, such as an adhesive, a string or cable, or a bioscaffold material.

In this design, the respective filter elements 426a, 426b, 426c cooperate to define a generally constant outer diameter 516 between a proximal end 518 of the first filter element 426a and a distal end 520 of the third filter element 426c. The substantially constant outer diameter 516 of the filter elements 426a, 426b, 426c improves the sealing connection between the embolic protection device 420 and the blood vessel 22, thereby reducing the number of emboli 24 that flow past the embolic protection device 420. Furthermore, the connections between the respective filter elements 426a, 426b, 426c prevent the individual filter elements from undesirably turning within the blood vessel 22 and otherwise stable the embolic protection device 420.

The first filter element 426a defines a first plurality of openings 522 so that the first filter element 426a is designed to capture relatively large emboli 24a. Additionally, the second filter element 426b defines a second plurality of openings 524 that are smaller than the first plurality of openings 522 so that the second filter element 426b is designed to capture medium-sized emboli 24b. Similarly, the third filter element 426c defines a third plurality of openings 526 that are smaller than the second plurality of openings 524 so that the third filter element 426c is designed to capture relatively small emboli 24c. As with the design shown in FIG. 2, the varying-size openings in the three filter elements 426a, 426b, 426c are beneficial for reducing the cross-sectional area of the filter 426 when the emboli 24 are trapped therewithin. In other words, each of the filter elements 426a, 426b, 426c is able to collect a generally equal volume of emboli 24, thereby equally distributing the emboli 24 among the filter elements 426a, 426b, 426c.

The center core wire 500 of the embolic protection device 420 guides the respective filter elements 426a, 426b, 426c within the blood vessel 22 and properly positions the elements 426a, 426b, 426c with respect to each other. For example, each of the filter elements 426a, 426b, 426c includes a sliding sleeve 528, 530, 532 attached to the distal end thereof 534, 536, 520 that receives and that is freely slidable along the center core wire 500. Therefore, the sliding sleeves 528, 530, 532 are able to slide along the center core wire 500 during deployment into the blood vessel 22 and during extraction therefrom, as will be discussed in further detail below. Furthermore, the sliding sleeves 528, 530, 532 radially position the filter elements 426a, 426b, 426c within the blood vessel 22 during emboli collection.

Figure 17:
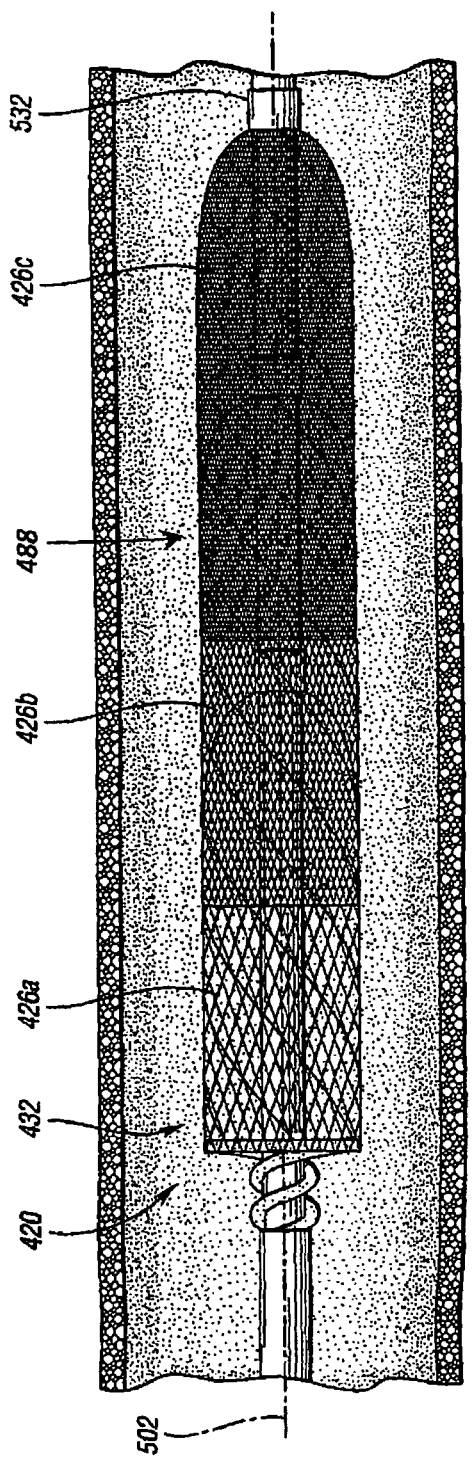
FIG. 17 is an environmental side view of the embolic protection device from FIG. 16 in a collapsed state for extraction from the blood vessel.

The embolic protection device 420 is moved between an expanded state 434 (shown in FIG. 16) and a collapsed state 432 (FIG. 17) by a control sleeve 538 and a connecting member 540. For example, the control sleeve 538 receives the center core wire 500 and is rotatable thereon to adjust the embolic protection device 420 between the expanded state 434 and the collapsed state 432. More specifically, the control sleeve 538 is connected to the proximal end 518 of the first filter element 426a by the connecting member 540 so that the proximal ends of the filter elements 426a, 426b, 426c each rotate about the center core wire 500 along with the control sleeve 538. The respective sliding sleeves 528, 530, 532 at the distal ends of the filter elements 426a, 426b, 426c are preferably disposed around the center core wire 500 so that they are permitted to slide axially therealong but not permitted to rotate therearound. For example, the sliding sleeves 528, 530, 532 may each have tabs extending into slots formed along the length of the center core wire 500 to prevent rotation of the sliding sleeves 528, 530, 532. Therefore, as the proximal portions of the filter elements 426a, 426b, 426c each rotate about the center core wire 500, the sliding sleeves 528, 530, 532 and the distal portions of the filter elements 426a, 426b, 426c are generally prevented from rotating about the center core wire 500, thereby causing the embolic protection device 420 to twist and collapse into an extraction position 488 as shown in FIG. 17.

In an alternative design, the filter elements 426a, 426b, 426c include frame portions made of a relatively elastic material, such as a super elastic metal, to ease the opening and closing of the embolic protection device 420. In yet another design, a delivery sleeve and/or an extraction sleeve are included to deliver and extract the emboli protection device 420, as described above.

It is therefore intended that the foregoing detailed description be regarded as illustrative rather than limiting, and that it be understood that it is the following claims, including all equivalents, that are intended to define the spirit and scope of this invention.

What is claimed is:

1. An embolic protection device for filtering emboli in a body vessel, the device comprising:
   a filter having a plurality of openings formed therethrough, the filter having an expanded state and a collapsed state, wherein the filter has a proximal expandable end and a distal non-expandable end;
   a delivery element comprising a delivery sleeve, the delivery sleeve configured to be movable with respect to the filter between a delivery position, where the delivery sleeve is disposed about at least a portion of the filter so that the filter is in the collapsed state, and a non-delivery position, where the delivery sleeve is located proximally from the proximal expandable end of the filter, the delivery sleeve having a proximal end and a distal end, each of the proximal and distal ends of the delivery sleeve having a first position in the delivery position and a second position in the non-delivery position; and
   an extraction element separate from the delivery sleeve and configured to be movable with the filter and independently of the filter between a non-extraction position, where the extraction element is located distally of the distal non-expandable end of the filter, and an extraction position, where the extraction element is disposed around at least a portion of the filter so that the filter is in the collapsed state, the extraction element including a proximal end and a distal end, each of the proximal and distal ends of the extraction element having a first position in the non-extraction position and a second position in the extraction position, the extraction element being movable relative to the delivery sleeve, wherein the extraction element is located distally from the filter when the delivery sleeve is disposed about at least a portion of the filter and wherein the delivery sleeve is located proximally from the filter when the extraction element is disposed around at least a portion of the filter.

2. An embolic protection device as in claim 1, wherein the extraction element includes an extraction sleeve.

3. An embolic protection device as in claim 1, wherein the extraction element includes an extraction wire defining a loop.

4. An embolic protection device as in claim 3, wherein the extraction wire defines a plurality of closed loops.

5. An embolic protection device as in claim 4, wherein each of the plurality of loops is movable with respect to each other.

6. An embolic protection device as in claim 3, wherein the extraction wire defines a coiled wire.

7. An embolic protection device as in claim 1, wherein the filter includes a first filter element and a second filter element spaced apart from each other.

8. An embolic protection device as in claim 7, wherein the first filter element defines a plurality of first filter openings, the second filter element defines a plurality of second filter openings, and each of the first filter openings are larger than each of the second filter openings.

9. An embolic protection device as in claim 7, wherein the filter includes a third filter element spaced apart from the first and the second filter elements.

10. An embolic protection device as in claim 1, further comprising:
a filter control wire coupled with the filter and configured to control the position thereof;
an extraction control wire coupled with the extraction element and configured to control the position thereof; and
a delivery control wire coupled with the delivery element and configured to control the position thereof.

11. An embolic protection device as in claim 10, wherein the filter control wire is a hollow wire defining a conduit receiving at least a portion of the extraction control wire and at least a portion of the delivery control wire.

12. An embolic protection device as in claim 10, wherein an outer diameter of the filter control wire is substantially greater than an outer diameter of the extraction control wire and is substantially greater than an outer diameter of the delivery control wire.

13. An embolic protection device for filtering emboli in a body vessel, the device comprising:
a filter having a plurality of openings formed therethrough, the filter having an expanded state and a collapsed state, wherein the filter has a proximal expandable end and a distal non-expandable end;
a delivery element comprising a delivery sleeve, the delivery sleeve configured to be movable with respect to the filter between a delivery position, where the delivery sleeve is disposed about at least a portion of the filter so that the filter is in the collapsed state, and a non-delivery position, where the delivery sleeve is located proximally from the proximal expandable end of the filter the delivery sleeve having a proximal end and a distal end, each of the proximal and distal ends of the delivery sleeve having a first position in the delivery position and a second position in the non-delivery position; and
an extraction element separate from the delivery sleeve and configured to be movable with the filter and independently of the filter between a non-extraction position, where the extraction element is located distally of the distal non-expandable end of the filter, and an extraction position, where the extraction element is disposed around at least a portion of the filter so that the filter is in the collapsed state, the extraction element including a proximal end and a distal end, each of the proximal and distal ends of the extraction element having a first position in the non-extraction position and a second position in the extraction position,
wherein the extraction element is located distally from the filter when the delivery sleeve is disposed about at least a portion of the filter and wherein the delivery sleeve is located proximally from the filter when the extraction element is disposed around at least a portion of the filter,
wherein the filter includes a first filter element and a second filter element spaced apart from each other,
wherein the first filter element defines a plurality of first filter openings and the second filter element defines a plurality of second filter openings, wherein the first filter openings are decreasing in size from a proximal portion to a distal portion of the first filter and the second filter openings are decreasing in size from a proximal portion to a distal portion of the second filter.

14. An assembly for removing emboli from a body vessel, the assembly comprising:
an inflatable catheter having a deflated state to facilitate delivery of the inflatable catheter within the body vessel and an expanded state to facilitate expansion of a wall of the body vessel, thereby potentially releasing the emboli into the body vessel;
an outer catheter for delivering the inflatable catheter into the body vessel;
an embolic protection device positioned distally of the inflatable catheter for collecting the emboli, the embolic protection device including:
a filter having a plurality of openings formed therethrough, the filter having an expanded state and a collapsed state, wherein the filter has a proximal expandable end and a distal non-expandable end;
a delivery element comprising a delivery sleeve, the delivery sleeve configured to be movable with respect to the filter between a delivery position, where the delivery sleeve is disposed about at least a portion of the filter so that the filter is in the collapsed state, and a non-delivery position, where the delivery sleeve is located proximally from the proximal expandable end of the filter, the delivery sleeve having a proximal end and a distal end, each of the proximal and distal ends of the delivery sleeve having a first position in the delivery position and a second position in the non-delivery position; and
an extraction element separate from the delivery sleeve and configured to be movable with the filter and independently of the filter between a non-extraction position, where the extraction element is located distally of distal non-expandable end the filter, and an extraction position, where the extraction element is disposed about at least a portion of the filter so that the filter is in the collapsed state, the extraction element including a proximal end and a distal end, each of the proximal and distal ends of the extraction element having a first position in the non-extraction position and a second position in the extraction position, the extraction element being movable relative to the delivery sleeve, wherein the extraction element is located distally from the filter when the delivery sleeve is disposed about at least a portion of the filter and wherein the delivery sleeve is located proximally from the filter when the extraction element is disposed around at least a portion of the filter.

15. An assembly as in claim 14, wherein the filter of the embolic protection device includes a first filter element and a second filter element spaced apart from each other.

16. An assembly as in claim 14, the embolic protection device further including:
  a filter control wire coupled with the filter and configured to control the position thereof;
  an extraction control wire coupled with the extraction element and configured to control the position thereof; and
  a delivery control wire coupled with the delivery element and configured to control the position thereof.

* * * * *